US010894983B2

(12) United States Patent
Ritter et al.

(10) Patent No.: US 10,894,983 B2
(45) Date of Patent: Jan. 19, 2021

(54) METHODS AND PRIMER SETS FOR HIGH THROUGHPUT PCR SEQUENCING

(71) Applicant: HS DIAGNOMICS GMBH, Berlin (DE)

(72) Inventors: Julia-Marie Ritter, Berlin (DE); Volkhard Seitz, Berlin (DE); Steffen Hennig, Berlin (DE); Michael Hummel, Berlin (DE)

(73) Assignee: HS DIAGNOMICS GMBH, Berlin (DE)

( * ) Notice: Subject to any disclaimer, the term of this patent is extended or adjusted under 35 U.S.C. 154(b) by 367 days.

(21) Appl. No.: 14/654,537

(22) PCT Filed: Dec. 20, 2013

(86) PCT No.: PCT/EP2013/077763
§ 371 (c)(1),
(2) Date: Jun. 21, 2015

(87) PCT Pub. No.: WO2014/096394
PCT Pub. Date: Jun. 26, 2014

(65) Prior Publication Data
US 2015/0337368 A1  Nov. 26, 2015

(30) Foreign Application Priority Data

Dec. 23, 2012 (EP) .................................. 12199315
Jul. 4, 2013 (EP) .................................. 13175199

(51) Int. Cl.
*C12Q 1/68* (2018.01)
*C12Q 1/6874* (2018.01)
*C12Q 1/6848* (2018.01)
*C12Q 1/6853* (2018.01)
*C12Q 1/6869* (2018.01)

(52) U.S. Cl.
CPC ......... *C12Q 1/6874* (2013.01); *C12Q 1/6848* (2013.01); *C12Q 1/6853* (2013.01); *C12Q 1/6869* (2013.01)

(58) Field of Classification Search
CPC .. C12Q 1/6848; C12Q 1/6853; C12Q 1/6869; C12Q 2525/161; C12Q 2525/191
See application file for complete search history.

(56) References Cited

U.S. PATENT DOCUMENTS

2009/0155859 A1* 6/2009 Nelson ................. C12Q 1/6848
435/91.53
2011/0207134 A1* 8/2011 Faham ................. C12Q 1/6886
435/6.11

FOREIGN PATENT DOCUMENTS

WO    WO 91/15601    10/1991
WO    WO 99/20798     4/1999

OTHER PUBLICATIONS

Baetens, M ., et al. Applying Massive parallel sequencing to molecular daignosis of Marfan and Loeys-Dietz syndromes. Human Mutation, vol. 32, No. 9, p. 1053-1062, 2011.*
Gholami, M et al. A tailed PCR procedure for cost-effective, two-order multiplex sequencing of candidate genes in ployploid plants. Plant Biotechnology Journal, vol. 10, p. 635-645, 2012.*
Adam Levy/Amplicon Ltd. two-temperature tagged (2T-TA) PCR for elinmination of false positives due to amplicon contamiantion. Research Dislosire, Mason publications, Hampshire, GB, vol. 499, No. 7, 2005.*
Machteld Baetens et al:"Applying massive parallel sequencing to molecular diagnosis of Marfan and Loeys-Dietz syndromes", Human Mutation, vol. 32, No. 9, Sep. 20, 2011(Sep. 20, 2011), pp. 1053-1062.
Adam Levy/ Amplion Ltd:"Two-temperature tagged (2T-TA) PCR for elimination of false positives due to amplicon contamination", Research Disclosure, Mason Publications, Hampshire, GB, vol. 499,No. 7, Oct. 14, 2005 (Oct. 14, 2005).
Schuelke M, "An economic method for the fluorescent labeling of PCR fragments," Nat Biotechnol. Feb. 2000;18(2):233-4.
Baetens M et al, "Applying massive parallel sequencing to molecular diagnosis of Marfan and Loeys-Dietz syndromes", Hum Mutat. Sep. 2011;32(9):1053-62.

* cited by examiner

Primary Examiner — David C Thomas
(74) Attorney, Agent, or Firm — JMB Davis Ben-David

(57) ABSTRACT

Described herein is a method for amplifying a target nucleic acid sequence $t_a$-$t_C$-$t_V$-$t_C$-$t_n'$ comprising a first amplification using a first primer pair with sequence $m_a$-K-$p_C$ and $m_a$-K'-$p_C'$, and a subsequent second amplification using a second primer pair with sequence $a_L$-$a_P$-$a_K$ and $a_L'$-$a_P'$-$a_K'$, wherein $p_C$ is the same sequence as sequence element $t_C$, $p_C$ and $p_C'$ are 8 to 40 nucleotides in length, K comprises a 3'-terminal sequence k1-k2-s, s is a mismatch sequences preventing PCR bias, $a_K$ is the same sequence as sequence element $k_1$, $a_P$-$a_K$ hybridize to a contiguous sequence on sequence element $m_a$-K, $k_1$ is 2 to 9 nucleotides in length, $a_L$ and $a_L'$ can be any sequence, and $t_V$ is a variable region within the target nucleic acid sequence. Also described are collections of primer sets for use in the method of the invention.

10 Claims, 4 Drawing Sheets
Specification includes a Sequence Listing.

METHODS AND PRIMER SETS FOR HIGH THROUGHPUT PCR SEQUENCING

CROSS-REFERENCE TO RELATED APPLICATIONS

This is the U.S. National Stage of International Application No. PCT/EP2013/077763, filed Dec. 20, 2013, which was published in English under PCT Article 21(2), which in turn claims the benefit of EP Patent Application Nos. 12199315.8, filed Dec. 23, 2012 and 13175199.2 filed Jul. 4, 2013.

Innovative techniques have been recently developed that allow the parallel generation of millions of sequence reads in a single run. High-dimensional data derived from this "next generation" or high throughput sequencing (NGS or HTS) may be used to resolve the biological variability within a single individual or within a population to a hitherto unknown precision and depth. Very sensitive techniques, however, bear the high risk of (cross-) contaminations from various sources. In order to avoid misinterpretation of NGS/HTS data, methods are needed that (i) prevent the amplification of potentially contaminating sequences and/or (ii) allow detecting the presence of contaminating sequences. The prevention of contaminations, in cooperation with identification of potential residual contaminations, is crucial for sensitive and reliable NGS diagnostics.

One major source for contamination is a two-step PCR amplification strategy, which is frequently used to generate PCR libraries suitable for NGS sequencing (Baetens et al., Human Mutation 32, 1053-1062 (2011)). In the first amplification reaction, the target nucleic acid sequence is amplified using specific primers flanked by a tail sequence (designated as $m_a$ in the context of the present specification; e.g. a M13 or T7 tail). Subsequently, a second (adaptor) primer pair amplifies the first amplificate producing the second amplificate, which can be used for sequencing. In the second amplification reaction, nucleic acid sequences required for NGS sequencing are introduced, employing primers complementary at their 3' end to the tail sequence of the first amplification primers. To make this approach more cost-efficient, multiplexing of several samples for NGS sequencing can be performed (Baetens, ibid.) by introducing so-called barcodes or multiplex-identifiers in the middle or close to the 5' end of the second amplification primers.

An overview showing potential sources of contamination is given in the table overleaf. Fields C and D are of most relevance for the present invention. A two-step amplification strategy shows a high probability for cross-contamination by carry-over of amplicons from the first PCR to the re-amplification (C) due to the high number of amplicons generated in the first amplification reaction. Furthermore, PCR products of a second amplification may contaminate other second amplification reactions (D). In the case of amplicon isolation by gel extraction or PCR-purification kits, the risk of contamination is even higher.

TABLE 1

Sources of cross-contamination and its prevention in a two-step PCR setting for NGS library generation. A & B: Contaminations of the first amplification by PCR products derived from another first or second amplification can be prevented by the UTP/UNG system and detected by tail- or adaptor-specific primers (U.S. Pat. No. 5,035,996, also published as EP0401037, U.S. Pat. No. 6,844,155B2, U.S. Pat. No. 7,914,986B2). C & D: Contaminations of the second amplification by PCR products derived from another first or second amplification can be prevented and detected by the "double contamination protection" described in the present invention.

| Type of contamination | Timepoint of contamination | |
|---|---|---|
| | First amplification PCR mix | Second amplification PCR mix |
| $1^{st}$ amplification PCR product | (A) Prevention: UTP/UNG System Detection: PCR with first. amplification tail-specific primers | (C) Prevention and detection: Double contamination protection (this invention) |
| $2^{nd}$ amplification PCR product | (B) Detection: PCR with first or second amplification tail- or adaptor-specific primers. Prevention: UTP/UNG System | (D) Prevention and detection: Double contamination protection (this invention) |

The objective of the present invention is to (i) avoid and/or to (ii) detect PCR-based contamination in applications employing massive parallel sequencing (NGS/HTS) techniques. This objective is attained by the subject matter of the independent claims.

Terms and Definitions

Nucleic acid sequences are given from 5' to 3' end. A sequence tract in the context used herein refers to a contiguous sequence; a sequence tract designator is a letter, optionally having a subscript or superscript, representing a sequence tract. $k_1$, $k_1'$, $k_2$, $k_2'$, s and s' are examples for sequence tract designators. Where sequences are given as a sequence of sequence tract designators, such sequences are understood to be ordered similarly in 5' to 3' order. A sequence tract is also called a sequence element.

Nucleic acid target sequences may be DNA or RNA; in case of RNA being the target sequence for amplification and sequencing, RNA is transcribed into cDNA (by reverse transcriptase) prior to amplification.

A "primer" in the context of the present specification refers to a single stranded DNA- or nucleic acid analogue building block-oligomer having a length between 8 and 100 nucleotides.

"Capable of forming a hybrid" in the context of the present invention relates to sequences that are able to bind selectively to their target sequence under the conditions of a PCR or sequencing reaction (for example, 10 mmol/l Tris-HCl pH 8.3; 100 mmol/l KCl; 1.5 mmol/l $MgCl_2$; 0.2 mmol/l dNTP, each; primer annealing temperature of 40° C. to 68° C.). Such hybridizing sequences may be contiguously reverse-complimentary to the target sequence, or may comprise gaps, mismatches or additional non-matching nucleotides. The minimal length for a sequence to be capable of forming a hybrid depends on its composition, with C or G nucleotides contributing more to the energy of binding than A or T/U nucleotides, and on the backbone chemistry, with some modifications such as LNA having significantly higher binding energy and thus, shorter minimal lengths, compared to DNA.

"Nucleotide" in the context of the present invention is a nucleic acid or nucleic acid analogue building block, an oligomer of which is capable of forming selective hybrids with an RNA or DNA sequence on the basis of base pairing. The term nucleotides in this context includes the classic ribonucleotide building blocks adenosine, guanosine, uridine (and ribosylthymine), cytidine, and the classic deoxyribonucleotides deoxyadenosine, deoxyguanosine, thymidine, deoxyuridine and deoxycytidine. The term nucleotides further includes analogues of nucleic acids, such as phosphorotioates, 2'O-methylphosphothioates, peptide nucleic acids (PNA; N-(2-aminoethyl)-glycine units linked by peptide linkage, with the nucleobase attached to the alpha-carbon of the glycine) or locked nucleic acids (LNA; 2'O, 4'C methylene bridged RNA building blocks). A primer sequence as used in the context of the present specification may be composed of any of the above nucleotides, or mixtures thereof. In some embodiments, a primer sequence is composed of deoxynucleotides, with the last (from the 3' position) 1, 2, 3 or 4 internucleotide bonds being phosporothioates. In certain embodiments, the last 4, 3, 2 or 1 nucleotides (counting from the 3' position) are LNA nucleotide analogues. In certain embodiments, the second nucleotide from the 3' position is a LNA nucleotide analogue. In certain embodiments, the second and third nucleotide from the 3' position is a LNA nucleotide analogue.

All of the US patents and US applications identified by number in the present specification are incorporated herein by reference.

SUMMARY OF THE INVENTION

The present invention provides guidelines for the design of three synergistically acting primer elements (designated generally as K-box with a capital "K", subdivided into a k-box (written with a lower case "k") for the forward primers and a k'-box for the reverse primers respectively) which in combination greatly improves the accuracy of PCR library preparations that can be analysed by methods including, but not restricted to, next generation sequencing (NGS).

The method of the invention makes use of two primer pairs. The first or initial primer pair amplifies the target sequence generating a first amplificate. Subsequently, a nested second (adaptor) primer pair amplifies the first amplificate producing the second amplificate, which can be used for sequencing.

For the analysis of a plurality of samples in parallel, the invention introduces the use of "sets" of individualized primer pairs for the first and second amplification to avoid cross-contamination, i.e. for each individual sample a different set is used. Thereby, a specific second primer pair is designed to only work together with a specific first primer pair within an individual set. The first and second primer pairs of an individualized primer set comprise a specially designed sequence tract referred to as K-box (K). Each K-box is specific for an individual primer set. The K-box of the (initial) primers for the first amplification step can comprise different elements $k_1$, $k_1'$, $k_2$, $k_2'$, s and s'. As explained in detail below, s/s' prevent PCR bias, $k_2/k_2'$ serve to detect contaminations and $k_1/k_1'$, which are also present in the K-box of the second amplification primers, prevent contamination. Importantly, matching $k_1/k_1'$ sequences enable the second primer pair to amplify the first amplificate only if the matching $k_1/k_1'$ sequences were comprised in the first primer of the same set that was used to generate the first amplificate. Primer pairs are arranged in corresponding and matching sets. A number of sets (e.g. set 1-300) represent a collection. A collection with N sets will allow processing N different samples without cross-contaminations in the second amplification reactions.

All initial primers of the first amplification step of a collection amplify the same target sequence. Different collections, amplifying different target sequences (i.e. in a multiplex PCR), may be combined as a multiplex-collection.

Definition of Frequently Used Terms

| Term | Description |
| --- | --- |
| Set | Within an individual set, a specific second primer pair is designed to work only together with a specific first primer pair. |
| Collection | A number of sets represent a collection. |
| Multiplex collection | A combination of different collections amplifying different target sequences. |

DETAILED DESCRIPTION OF THE INVENTION

Overview of the target and primer sequence tracts

Short description of primer and sequence tract abbreviations

| Abbreviation | Description |
| --- | --- |
| Target sequence tracts | |
| $t_n$-$t_C$-$t_V$-$t_C'$-$t_n'$ | Different sequence tracts of the target nucleic acid sequence. |
| $t_C/t_C'$ | Target sequence tract used for target-specific primer binding |
| $t_V$ | Target nucleic acid sequence of interest. |
| $t_n/t_n'$ | Sequence tracts of the target gene located in 5' and 3' position of $t_C/t_C'$, respectively. |
| Sequence tracts of the primers used for first amplification | |
| $m_a/m_a'$ | Tail sequence (e.g. M13) of first amplification primer. |
| $m_a$-K/$m_a'$-K' | Tail sequence + K-box of first amplification primer. |
| $p_C/p_C'$ | First amplification primer sequence tracts which provide target specificity. |
| Sequence tracts of the primers used for second amplification | |
| $a_P/a_P'$ | Second amplification primer sequence tracts which hybridize to $m_a/m_a'$. |
| $a_L/a_L'$ | Second amplification primer sequence tracts for NGS sequencing. |

-continued

| Abbreviation | Description |
|---|---|
| \multicolumn{2}{K-box} | |
| K-box | Comprises the sequence tracts $k_1/k_1'$, $k_2/k_2'$, S/S'. |
| k-box | K-box of the left (up-stream) first and second amplification primer. |
| k'-box | K-box of the right (down-stream) first and second amplification primer. |
| $k_1/k_1'$ | K-box elements of first and second amplification primers for suppression of contaminations. |
| $k_2/k_2'$ | K-box element of first amplification primers for detection of contaminations. |
| S/S' | K-box element present in first amplification primers to avoid a PCR bias possibly introduced by $k_1/k_1'$, $k_2/k_2'$. |

In general, the "prime" or apostrophe (') indicates that a sequence tract or element has a similar functional characteristic as its non-prime counterpart, but is located on a primer on the other side of the target sequence, and is understood to work in reverse direction.

The target nucleic acid sequences subject to amplification are described as $t_C$-$t_V$-$t_C'$. Therein, $t_C/t_C'$ are the sequence tracts to which the forward (left) and reverse (right) primary amplification primer hybridizes, respectively. $t_V$ is a region of interest (the sequenced part likely to contain the variability that the sequencing seeks to elucidate) within a target nucleic acid sequence. Furthermore the target nucleic acid sequence elements $t_n$ and $t_n'$ are located in 5' and 3' position, respectively, of $t_C$-$t_V$-$t_C'$. The target structure can also be described as $t_n$-$t_C$-$t_V$-$t_C'$-$t_n'$.

A primer for use in a method or collection of primers according to the invention is composed of at least two sequence tracts.

A left first or initial primer used in the first round of amplification comprises (from 5' to 3' OH-end) a sequence tract $m_a$-k-box (also designated as $m_a$-K) and a sequence tract $p_C$ (FIG. 1). Sequence tract $p_C$ provides target specificity, while $m_a$-K provides a non-target-specific sequence tract, parts or all of which can be used for hybridization of a second "adaptor" primer. Within $m_a$-K the sequence tract $m_a$ can comprise sequence elements necessary for sequencing purposes or consist of sequences such as M13, whereas the K-box comprises the K-box elements ($k_1/k_1'$, $k_2/k_2'$, s/s').

The left adaptor (second) primer comprises distinct sequence tracts, designated $a_L$ and $a_P$-$a_K$, which are used for the second amplification. $a_L$ and $a_P$ confer functional features for high throughput sequencing, e.g. template sequences for sequencing primers and/or for attachment of the amplificate to a solid surface such as a slide or a bead. Furthermore, $a_P$ can consist of a sequence such as M13. The sequence tract $a_K$ comprises $k_1$, which is a sequence element of the K-box.

The reverse or right primers, of both the initial and adaptor primers, comprise sequence tracts of similar characteristics, designated $m_a'$-k'-box (also designated as $m_a$-K') and $p_C'$ for the right initial (first) primer. The right adaptor (second) primer comprises the sequence tracts $a_L'$ and $a_P'$-$a_K'$ (FIG. 1).

Sequence elements $a_L$ and $a_P$ are used for sequencing purposes, such as, by way of non-limiting example, sequencing primer hybridization sites and/or solid support attachment sites. Methods for high-throughput sequencing are well known in the art and include so called "Illumina" bridge PCR-sequencing methods, shown inter alia in US2011045541A1, US2005100900A1, US2002055100A1; pyrosequencing, shown inter alia in U.S. Pat. Nos. 6,274,320, 7,244,567, 7,264,929; 7,323,305 and 7,575,865; "2 base encoding" technology (U.S. Pat. Nos. 4,883,750, 5,750, 341) and others. Further relevant methods for high-throughput sequencing and applications are described in the following manuscripts:

Robustness of Amplicon Deep Sequencing Underlines Its Utility in Clinical Applications. Grossmann et al. J Mol Diagn. 2013 May 14. doi:pii: S1525-1578(13)00057-3. PMID:23680131; Solid-State and Biological Nanopore for Real-Time Sensing of Single Chemical and Sequencing of DNA. Hague et al. Nano Today. 2013 February; 8(1):56-74. PMID:23504223; Next-generation sequencing—feasibility and practicality in haematology. Kohlmann et al. Br J Haematol. 2013 March; 160(6):736-53. doi: 10.1111/bjh.12194. Epub 2013 Jan. 7. PMID:23294427; Progress in ion torrent semiconductor chip based sequencing. Merriman et al. Electrophoresis. 2012 December; 33(23):3397-417. doi: 10.1002/elps.201200424. Erratum in: Electrophoresis. 2013 February; 34(4):619. PMID:23208921; Comparison of next-generation sequencing systems. Liu et al. J Biomed Biotechnol. 2012; 2012:251364. doi: 10.1155/2012/251364. PMID:22829749; Current state-of-art of sequencing technologies for plant genomics research. Thudi M et al. Brief Funct Genomics. 2012 January; 11(1):3-11. doi: 10.1093/bfgp/elr045. PMID:22345601; Integration of next-generation sequencing into clinical practice: are we there yet? Kohlmann A et al. Semin Oncol. 2012 February; 39(1):26-36. doi: 10.1053/j.seminoncol.2011.11.008. PMID: 22289489.

The primers of the invention provide particular sequence elements (K-boxes), which greatly reduce the likelihood that such contaminations occur and enable the recognition of amplicon contaminations within the sequencing results. The K-box elements are designated $k_1$, $k_1'$, $k_2$, $k_2'$, s and s', and are selected by bioinformatics methods as one single K-box, the selection being made not to perform mismatches with the 3' ends of the primers employed. For clarification of their mode of action, however, the three K-box elements are outlined in the following in detail separately:

Role of $k_1$ and $k_1'$ K-box elements and mode of action:

The $k_1/k_1'$ sequences are designed to prevent contamination from previous amplification reactions. As outlined in FIG. 1 the forward primer of the first PCR is composed of (i) a target-specific proportion $p_C$, (ii) and the K-box sequence element $k_1$, which is specific for each primer set and (iii) and a sequence element $m_a$. The reverse primer of the first PCR is composed in the same way but in reverse-complement fashion.

A specific $k_1$ and/or $k_1'$ element is used for a particular reaction and is varied when the amplification reaction is performed repeatedly. In other words, if a routine diagnostic amplification reaction (e.g. the analysis of T-cell receptor beta (TCRB) rearrangements or the analysis of cancer genes) is performed a plurality of times in the same laboratory, primers using different $k_1/k_1'$ elements may be used for each individual experiment until all variations of $k_1$ and $k_1'$ have been consumed. The 3' end of the second (or adaptor) primer is chosen to hybridize to $k_1$ or $k_1'$, respectively, along the entire length of $k_1$ (or $k_1'$). Thus, pairs of first and second primers are formed, where the "left" adaptor primer hybridizes to sequence tract $k_1$ that was generated by the "left" initial primer, and the "right" adaptor primer hybridizes to the sequence tract $k_1'$ that was generated by the "right" initial primer. In order to allow full hybridization, the adaptor primer will hybridize not necessarily only to the tract generated by $k_1$ (or $k_1'$), but—if $k_1$ (or $k_1'$) does not provide sufficient length of hybridization tract—for the hybridization temperature selected for the reaction—also to a sequence tract adjacent to $k_1$ (or $k_1'$) on its 5' end, namely $m_a$ and $m_a'$ (see FIG. 1).

As example, five samples are processed in parallel with five different sets of first (initial) and second (adaptor) primers with a $k_1/k_1'$ element combination specific for each of the five samples. In the case of contamination of the second PCR of sample 2 with PCR products derived from the primary PCR of sample 1, the mismatch between the $k_1$ and/or $k_1'$ element of the PCR product of sample 1 and the different $k_1$ and/or $k_1'$ elements of the sample 2 primers will prevent the amplification of the contaminating material.

Both, $k_1$ and $k_1'$ can be of 1, 2, 3, 4, 5, 6, 7, 8, 9 or more bases in length. As shown in the proof of principle example below (Table 4) even a $k_1/k_1'$ sequence of one base reduces contamination. However since the number of permutations is relatively low and the discriminatory power (in the sense of contamination suppression) of a one-base mismatch not as great as that of longer mismatches, $k_1$ and $k_1'$ elements of greater length, for example 2, 3, 4, 5, 6, 7, 8 or 9 have broader utility (Examples are given in Tables 16-19).

Role of $k_2$ and $k_2'$ K-box elements and mode of action:

A further K-box element is a sequence element $k_2$ or $k_2'$, comprised in the sequence tract $m_a$-K or $m_a$-K', respectively, of the initial primer, but not in the corresponding sequence tract in the second amplification (adaptor) primer (FIG. 2). Hence, $k_2$ and $k_2'$ are characteristic of the initial primer only. In embodiments where $k_2$ (or $k_2'$) and $k_1$ (or $k_1'$) sequences are comprised in the initial primer, the $k_2$ (or $k_2'$) element is downstream (towards the 3' end) from the $k_1$ (or $k_1'$) sequence element (FIG. 2).

While $k_1$ and $k_1'$ lead to suppression of contaminations, the $k_2/k_2'$ sequences are designed to detect contamination from previous amplification reactions.

Therefore, as in the case of $k_1$ (or $k_1'$), the presence of $k_2$ (or $k_2'$) in specific variation (Examples are provided in Table 20) over a plurality of primer sets used at different times or for different samples in the same routine setting helps to detect contaminations and synergistically control the contamination suppression efficacy of $k_1/k_1'$.

Role of s and s' K-box elements and mode of action:

The K-box elements s/s' prevent a possible PCR bias dependent on $k_1/k_1'$ and $k_2/k_2'$ sequences as outlined below.

S separates the target-specific left initial primer sequence $p_C$ from the sequence tracts $k_2$ and/or $k_1$. s' separates the target-specific right initial primer sequence $p_C'$ from $k_2'$ and/or $k_1'$ (see FIG. 3-4). Since $k_1/k_1'$ and $k_2/k_2'$ vary among different primers used in subsequent amplifications, some variations of $k_2/k_2'$ and/or $k_1/k_1'$ may coincidentally match in their 3' end nucleotides the sequence of the target next to the hybridizing part of the initial primers $p_C$ or $p_C'$. The target sequence-matching tract of the initial primer would be longer for some targets than for others, leading to PCR bias resulting from higher annealing temperatures.

This problem is amplified if—as provided in some embodiments of the present invention—multiplex-collections are employed. A set within a multiplex collection addresses different target sequences for use in a multiplex PCR, but carries the same $k_1$ (and $k_1'$) and, optionally, $k_2$ (and $k_2'$) elements. Here, different annealing temperatures might introduce a PCR bias that may significantly skew any quantitative interpretation of the results.

Hence, in some embodiments a short (1, 2, 3 or 4 nucleotides) separator sequence S (s') is introduced into the k/k' sequence tract, immediately upstream of the $p_C/p_C'$ sequence tract, i.e., at the 3' terminal end of k/k'. s and s' are thus designed to prevent a hybrid formation with the template (target) sequence $t_n/t_n'$ adjacent to the primer-hybridizing sequence tract $t_C/t_C'$, as outlined in FIG. 3-4.

Advantages of Using Combined $k_1$, $k_2$, S and $k_1'$, $k_2'$, s' Sequence Elements:

The three K-box elements work synergistically to achieve the overall goal of preventing PCR-based contamination in applications employing NGS/HTS techniques.

Since the $k_2/k_2'$ elements are only present in the first amplification primers an eventual contamination can still be identified in the second amplification product. Thus, $k_2/k_2'$ elements determine and therefore control the contamination suppression efficiency of $k_1/k_1'$.

Furthermore, s/s' is the K-box family member that solves the problem of a possible PCR bias dependent on $k_1/k_1'$ and $k_2/k_2'$ sequences.

Finally, all three K-box elements together must be designed bioinformatically as one unit and optimized not to form hybrids (e.g. more than 6 bp match within 10 bp) that might lead to mispriming with any primer sequence but especially at the 3' ends of the primers employed.

Different Aspects of the Invention:

According to a first aspect of the invention, a method for amplifying a target nucleic acid sequence $t_C$-$t_V$-$t_C'$ comprised within a sequence tract $t_n$-$t_C$-$t_V$-$t_C'$-$t_n'$ is provided, said method comprising conducting a plurality of polymerase chain reaction (PCR) amplification reactions. In other words, the invention is directed toward a method of repeatedly amplifying or sequencing the same target sequence (albeit in variation that may occur within a sequence tract of interest designated $t_V$). Each reaction comprises two PCR amplification steps: a first amplification step, in which a target nucleic acid sequence is amplified using a first ("initial") primer pair, and includes the reactants known to the skilled artisan as necessary for conducting a PCR reaction, i.e. nucleoside triphosphates (ATP, GTP, TTP, CTP), a suitable buffer and thermostable polymerase such as Taq polymerase. This initial primer pair is composed of a left (forward) first ("initial") PCR primer having a sequence $m_a$-K-$p_C$ composed of two sequence elements $m_a$-K and $p_C$ in 5'-3' orientation, and a right (reverse) initial primer having a sequence $m_a$-K'-$p_C'$, similarly oriented from 5' to 3'. The product of the first amplification set is a first amplificate, comprising the target nucleic acid sequence flanked on either side by sequence tracts $m_a$-K and $m_a$-K', respectively (FIG. 1).

The sequence $t_C$-$t_V$-$t_C'$ constitutes the amplified region of the target, whereas the short sequence elements $t_n$ and $t_n'$ are flanking regions that define the selection of sequence elements s and s' in the primer set.

The method of the invention further comprises a second PCR amplification step, whereby a first amplificate is re-amplified using a second ("adaptor") primer pair composed of a left (forward) second ("adaptor") PCR primer having a sequence $a_L$-$a_P$-$a_K$ composed of the sequence elements $a_L$, $a_P$ and $a_K$ in 5'-3' orientation and a right (reverse) second ("adaptor") PCR primer having a sequence $a_L'$-$a_P'$-$a_K'$. Again, the reactants necessary for conducting a PCR reaction, i.e. nucleoside triphosphates, a suitable buffer and thermostable polymerase are present. The product of the second amplification is a second amplificate (FIG. 1).

Within the first primer pair, $p_C$ displays the same sequence as the target sequence element $t_C$, $p_C'$ is the reverse complimentary sequence to $t_C'$. In other words, $p_C$ and $p_C'$ are the target-specific primer sequences that hybridize to the target and effect amplification. $p_C$ and $p_C'$ each independently from one another are 8 to 40 nucleotides in length.

Within the first primer pair, $m_a$-K comprises a k-box with the sequence element $k_1$, and $m_a$-K' comprises a k'-box with a sequence element $k_1'$. $k_1$ and $k_1'$ each independently from one another are a sequence 2, 3, 4, 5, 6, 7, 8 or 9 nucleotides in length. $k_1$ and $k_1'$ are not meant to hybridize to the target sequence. A first primer pair and a second primer pair with identical $k_1$ and $k_1'$ form a set. $k_1$ and $k_1'$ are the sequence elements that individualize different primer sets from one another. $k_1$ and $k_1'$ match the first "initial" and the second "adaptor" PCR primer pairs to one another within a set. Thus, $k_1$ and $k_1'$ of the first initial primer pair correspond to the sequence elements $a_k$ ($k_1$) and $a_{K'}$ ($k_1'$), respectively, in the second primer pair (FIG. 1).

Furthermore, $m_a$-K comprises a sequence element S on its 3' terminus and $m_a$-K' comprises a sequence element s' on its 3' terminus. s and s' are mismatch sequences selected not to form a continuous hybrid sequence with sequence element $t_n$ and $t_n'$ and S and s' are independently 1, 2, 3, 4 or 5 nucleotides in length. As described in detail above, the effect of this element is to avoid an inadvertent rise of the annealing temperature of $p_C$ and $p_C'$ on the target in some primers dependent on $m_a$-K and/or $m_a$-K' sequences. This element helps to avoid PCR bias (FIG. 3-4).

Sequence tract $a_P$-$a_K$ hybridizes to a contiguous sequence on sequence element $m_a$-K, and $a_P'$-$a_K'$ hybridizes to a contiguous sequence on sequence element $m_a$-K'. In other words, $a_P$-$a_K$ (and its analogue $a_P'$-$a_K'$) is the sequence tract on the 3' terminal end of the adaptor primer that recognizes the initial primer.

$m_a$-K and $m_a$-K' can be of any length that fits their general purpose, but will generally be within the usual length of a primer target sequence, i.e. $m_a$-K and $m_a$-K' will be generally each independently from one another a sequence 10 to 40 nucleotides in length, in certain embodiments from about 15 to 30 nucleotides in length.

$a_L$ and $a_L'$ and also $a_P$ and $a_P'$ independently from one another can be any sequence that fits the general purpose of providing a sequence useful for sequencing the second amplificate, for example by providing a sequencing primer annealing target and/or a sequence for attaching the second amplificate to a chip or bead or any other surface-bound structure as may be useful in NGS/HTS sequencing.

$t_V$ is a variable region within said target nucleic acid sequence.

Additionally, according to this first aspect of the invention, a particular set of primers for each one of said plurality of amplification reactions is provided, for each of which the sequence of one of $k_1$ and $k_1'$ is different from the sequence of any other $k_1$ and $k_1'$, respectively, in any other set of the sets of primers. In other words, no particular sequence of $k_1$ and/or $k_1'$ occurs more than once in any set.

In some embodiments, $a_L$ and $a_L'$ are 5, 10, 15, 20, 25, 30, 35, 40, 45, 50, 55, 60, 65 or 70 nucleotides in length. In some embodiments, $p_C$ and $p_C'$ each independently from one another are 8, 10, 12, 14, 16, 18, 20, 21, 22, 23, 24, 25, 26, 27, 28, 29, 30, 32, 34, 36, 38 or 40 nucleotides in length.

Thus, in certain embodiments, $m_a$-K comprises a 3'-terminal sequence $k_1$-S, and $m_a$-K' comprises a 3'-terminal sequence $k_1'$-s'.

In certain embodiments, $m_a$-K comprises a sequence element $k_2$ 3'-terminal to sequence element $k_1$, and $m_a$-K' comprises a sequence element $k_2'$ 3'-terminal to sequence element $k_1'$ (FIG. 2). $k_2$ and $k_2'$ each independently from one another are 2, 3, 4, 5, 6 or 7 nucleotides in length. $k_2$ and $k_2'$ serve to individualize the first primer pair of the set from other first (initial) primers. $k_2$ and $k_2'$ have no complementary sequence elements on the second ("adaptor") primers. The second primers $k_1$ and $k_1'$ have complementary sequences to the first primers within one primer set.

In some embodiments, the primer set uses all three elements $k_1/k_1'$, $k_2/k_2'$ and s/s' (FIG. 3). Thus $m_a$-K comprises a 3'-terminal sequence $k_1$-$k_2$-S, and $m_a$-K' comprises a 3'-terminal sequence $k_1'$-$k_2'$-s'. In some embodiments, $m_a$-K comprises a 3'-terminal sequence $k_1$-$k_2$-S, and $m_a$-K' comprises a 3'-terminal sequence $k_1'$-$k_2'$-s' and the first and/or second primer pairs have phosphorothiolated moieties on the last 1, 2, 3 or 4 internucleotide linkages at their 3' terminal end.

In certain embodiments, K comprises a 3'-terminal sequence $k_1$-$k_2$-S, and K' comprises a 3'-terminal sequence $k_1'$-$k_2'$-s', wherein
   $k_1$ and $k_1'$ each independently from one another are a sequence 2 to 9 nucleotides in length,
   $k_2$ and $k_2'$ each independently from one another are a sequence 2 to 7 nucleotides in length;
   s and s' are mismatch sequences selected not to form a continuous hybrid sequence with sequence element $t_n$ and $t_n'$, and s and s' are independently 1, 2, 3, 4 or 5 nucleotides in length,
   $a_k$ is the same sequence as sequence element $k_1$ and $a_{K'}$ is the same sequence as sequence element $k_1'$,
   $a_k$ and $a_{K'}$ are selected not to hybridize to $k_2$ and $k_2'$, respectively;
   $a_P$-$a_K$ hybridizes to a contiguous sequence on $m_a$-K and $a_P'$-$a_{K'}'$ hybridizes to a contiguous sequence on $m_a$-K'
   $p_C$, $p_C'$, $m_a$-K and $m_a$-K' each independently from one another are a sequence 10 to 40 nucleotides in length, and $a_L$ and $a_L'$ independently from one another can be any sequence.

In certain embodiments, $k_1$ and $k_1'$ each independently from one another are a sequence 5, 6, 7, 8 or 9 nucleotides in length, s and s' are each independently 2, 3, or 4 nucleotides in length, and/or $k_2$ and $k_2'$ each independently from one another are a sequence 2, 3, 4, 5 or 6 nucleotides in length.

In certain embodiments, for each particular set of primers, each $k_1$ is different from of any other $k_1$ and each $k_1'$ is different from any other $k_1'$, resulting in a specific combination of $k_1$ and $k_1'$ for each set, and/or each $k_2$ is different from of any other $k_2$ and each $k_2'$ is different from any other $k_2'$ resulting in a specific combination of $k_2$ and $k_2'$ for each set.

In some embodiments, the sets of primers comprise
   a left (forward) initial primer comprising a sequence element $p_C$ selected from any one of SEQ ID NO 001 to SEQ ID NO 045 and a right (reverse) initial primer comprising a sequence element $p_C'$ selected from any one of SEQ ID NO 046 to SEQ ID NO 058; and/or
   a left (forward) initial primer comprising a sequence element $p_C$ selected from any one of SEQ ID NO 189 to SEQ ID NO 232 and a right (reverse) initial primer comprising a sequence element $p_C'$ selected from any one of SEQ ID NO 233 to SEQ ID NO 246; and/or a left (forward) initial primer comprising a sequence element $m_a$ selected from any one of SEQ ID NO 059 to SEQ ID NO 085 and a right (reverse) initial primer comprising a sequence element $m_a$ selected from any one of SEQ ID NO 086 to SEQ ID NO 117; and/or a left (forward) adaptor primer comprising a sequence element $a_L$-$a_P$ selected from any one of SEQ ID NO 118 to SEQ ID NO 149 and a right (reverse) adaptor primer comprising a sequence element $m_a$ selected from any one of SEQ ID NO 150 to SEQ ID NO 182.

In certain embodiments, $k_1$ and $k_1'$ and/or $k_2$ and $k_2'$ (where $k_2$ and $k_2'$ are contained in the sequence) are selected not to hybridize to the sequence elements $t_n$ and $t_n'$ adjacent to the amplified sequence tract. In other words, $k_1$ and $k_1'$ and $k_2$ and $k_2'$ (where $k_2$ and $k_2'$ are contained in the sequence) are separate and distinct from a primer sequence directed toward target amplification. All k-box components solely and exclusively have the purpose of distinguishing the primer set, and thus preventing erroneous amplification of amplicon contaminations, as set forth above.

In some embodiments, the left initial primer, the right initial primer, the left adaptor primer and/or the right adaptor primer are characterized by one or several nuclease resistant nucleotide(s) or nuclease resistant internucleosidic bond(s) on or near (at position 1, 2, 3 and/or 4 counting from) the 3' terminus of the primers. In other words, the 3' end of the primer is protected against 3' exonuclease digestion by providing bonds that inhibit or resist the exonuclease activity.

In some embodiments, the nuclease resistant internucleosidic bond is a phosphorothioate bond. In some embodiments, the nuclease resistant nucleotide is a 2-O-methylated ribonucleotide. In some embodiments, the nuclease resistant nucleotide is an LNA building block (a 2'O, 4'C-methylene bridged RNA building block). In some embodiments, the nuclease resistant nucleotide is a 2-F-deoxyribonucleotide. In some embodiments, the nuclease resistant nucleotide is a 2-propyne-deoxyribonucleotide.

In some embodiments, the nuclease resistant nucleotide or nuclease resistant internucleosidic bond is the last internucleosidic bond counting from the 3' terminus of said primer(s). In some embodiments, the nuclease resistant nucleotide or nuclease resistant internucleosidic bond is located on position-1, -2, -3, and/or -4 counting from the 3' terminus of said primer(s). In some embodiments, the nuclease resistant nucleotide or nuclease resistant internucleosidic bond are located at position-1 and -2, in some embodiments at position-1 and -2 and -3, or in some embodiments at position-1 and -2 and -3 and -4.

For avoidance of doubt, in the sequence 5' GpApTxGyC 3', y marks the -1 position, x marks the -2 position, p marks the -3 and -4 position of the internucleosidic bonds, and C marks the position-1 and G marks the position-2 of the nucleotide counting from the 3' end.

According to one alternative of this first aspect of the invention, a method for sequencing a target sequence $t_C$-$t_V$-$t_C'$ comprised within a sequence tract $t_n$-$t_C$-$t_V$-$t_C'$-$t_n'$ is provided, said method comprising the steps of a. amplifying said target sequence by a method as outlined above in any of the aspects and embodiments provided, and b. sequencing said second amplificate including sequence elements $m_a$-K and/or $m_a$-K', yielding a set of readout sequences.

Methods of sequencing are known to the skilled artisan and include (but are not limited to) the methods described in the publications referenced above.

In some embodiments, the method for sequencing a target sequence further comprises the steps of c. aligning each member of said set of readout sequences to sequence element $m_a$-K and/or $m_a$-K' comprised in said initial primer, respectively, and d. assigning a value of 0 or 1 as a measure of contamination to each sequence of said set of readout sequences (e.g. the results of NGS sequencing of one sample), wherein complete alignment of a member of said set of readout sequences (i.e. a particular readout sequence) to said sequence element $m_a$-K or $m_a$-K' corresponds to the value of 0 (signifying no contamination for that particular set member), and incomplete alignment of a member of said set of readout sequences to said sequence element $m_a$-K or $m_a$-K' corresponds to 1 (signifying that this particular read was caused by a contamination); and (i) determining a percentage of contamination by adding all values assigned in step d), resulting in a value sum, and dividing said value sum by the total number of reads; and/or (ii) removing the sequences having a value of "1" from the sequence set.

Thus, if the set of readout sequences consists of 10.000 sequences, for 32 of which the sequence tract corresponding to $m_a$-K or $m_a$-K' does not align with the particular sequence expected (chosen) for the particular run, then a percentage of contamination of 32/10.000, resulting in 0.0032 or 0.32% is computed.

In other words, the method for sequencing a target sequence includes a step of validation or quality control, wherein all sequences obtained are checked for the presence of identifier sequences $k_2$, $k_2'$ and/or $k_1$, $k_1'$ ($k_1$, $k_1'$ can be relevant as identifier of the first amplification reaction, since $k_1$, $k_1'$ of the second amplification primer can be partially degraded in the second PCR by proof reading polymerases as outlined in detail in the proof of principle examples). Unexpected identifier sequences, or unexpected combinations thereof, are regarded as contamination.

For each amplification reaction, a different set of primers is used, the difference being in different sequence elements $k_1$, $k_1'$, $k_2$ and $k_2'$ or combinations thereof. In other words, the method comprises the steps of providing a set of primers for each sample of said plurality of samples, each set of primers comprising a pair of initial PCR primers comprising a left initial PCR primer having a sequence $m_a$-K-$p_C$ and a right initial primer having a sequence and $m_a$-K'-$p_C'$, and a pair of adaptor PCR primers comprising a left adaptor PCR primer having a sequence $a_L$-$a_P$-$a_K$ and a right adaptor PCR primer having a sequence $a_L'$-$a_P'$-$a_K'$.

According to another aspect of the invention, a set of primers for use in a method for amplifying or sequencing a target nucleic acid sequence according to the invention is provided, wherein each set of primers of said collection comprises i. a pair of initial PCR primers comprising a left (forward) initial PCR primer having a sequence $m_a$-K-$p_C$ and a right (reverse) initial primer having a sequence and $m_a$-K'-$p_C'$, and ii. a pair of adaptor PCR primers comprising a left adaptor PCR primer having a sequence $a_L$-$a_P$-$a_K$ and a right adaptor PCR primer having a sequence $a_L'$-$a_P'$-$a_K'$, wherein all sequence designators have the meaning outlined above, namely:

$p_C$ is the same sequence as sequence element $t_C$ and $p_C'$ is the reverse complimentary sequence to $t_C'$, K comprises a sequence element $k_1$ and a 3'-terminal sequence element S, and K' comprises a sequence element $k_1'$ and a 3'-terminal sequence element s', wherein $k_1$ and $k_1'$ each independently from one another are a sequence 2 to 9 nucleotides in length, s and s' are mismatch sequences selected not to form a continuous hybrid sequence with sequence element $t_n$ and $t_n'$, and s and s' are each independently 1, 2, 3, 4 or 5 nucleotides in length, $a_k$ is the same sequence as sequence element $k_1$ and $a_{K}'$ is the same sequence as sequence element $k_1'$, $a_P$-$a_K$ hybridizes to a contiguous sequence on $m_a$-K and $a_P'$-$a_K'$ hybridizes to a contiguous sequence on $m_a$-K'

$p_C$, $p_C'$, $m_a$-K and $m_a$-K' each independently from one another are a sequence 10 to 40 nucleotides in length, and $a_L$ and $a_L'$ independently from one another can be any sequence.

In some embodiments, K comprises a 3'-terminal sequence $k_1$-$k_2$-S, and K' comprises a 3'-terminal sequence $k_1'$-$k_2'$-s', wherein $k_2$ and $k_2'$ each independently from one another are a sequence 2 to 7 nucleotides in length, and $a_k$ and $a_{K}'$ are selected not to hybridize to $k_2$ and $k_2'$, respectively.

In certain embodiments, all sequence elements $a_P$ are the same and all sequence elements $a_P'$ are the same for a collection.

In one embodiment, a set of primers according to the invention (and intended for use in a method of the invention) comprises:

a left (forward) initial primer comprising a sequence element $p_C$ selected from any one of SEQ ID NO 001 to SEQ ID NO 045 and a right (reverse) initial primer comprising a sequence element $p_C'$ selected from any one of SEQ ID NO 046 to SEQ ID NO 058; and/or a left (forward) initial primer comprising a sequence element $p_C$ selected from any one of SEQ ID NO 189 to SEQ ID NO 232 and a right (reverse) initial primer comprising a sequence element $p_C'$ selected from any one of SEQ ID NO 233 to SEQ ID NO 246; and/or a left (forward) initial primer comprising a sequence element $m_a$ selected from any one of SEQ ID NO 059 to SEQ ID NO 085 and a right (reverse) initial primer comprising a sequence element $m_a$ selected from any one of SEQ ID NO 086 to SEQ ID NO 117; and/or a left (forward) adaptor primer comprising a sequence element $a_L$-$a_P$ selected from any one of SEQ ID NO 118 to SEQ ID NO 149 and a right (reverse) adaptor primer comprising a sequence element $m_a$ selected from any one of SEQ ID NO 150 to SEQ ID NO 182.

According to another aspect of the invention, a collection of sets of primers for use in a method for amplifying or sequencing a target nucleic acid sequence according to any of the preceding aspects and embodiments is provided, wherein each set adheres to the definition given for the previously defined aspect of the invention (a set of primers according to the invention), and wherein for all sets of primers comprised within said collection, all sequence elements $p_C$ are the same and all sequence elements $p_C'$ are the same. Furthermore, each set of primers is characterized by a different combination of $k_1$ and $k_1'$ from any other set of primers.

In other words: in each of these sets of primers, $k_1$ is different from any other $k_1$ and/or $k_1'$ is different from one of any other $k_1'$ in each of the other sets. In other words, each set has a unique K1/K1' combination.

In some embodiments of this aspect of the invention, where $k_2$ and $k_2'$ are present, for each said particular set of primers, one of $k_2$ and $k_2'$ are different from of any other $k_2$ and $k_2'$, respectively. In other words: each set of primers is characterized by a different combination of $k_1$, $k_1'$, $k_2$ and $k_2'$ from any other set of primers.

In certain embodiments, the collection of sets of primers according to the invention comprise 4, 8, 16, 24, 32, 40, 48, 56, 64, 72, 80, 160, 200, 256 or 1024 different sets of primers.

According to yet another aspect of the invention, a multiplex-collection (primer library) comprising a plurality of collections of sets of primers according to the invention is provided, whereby each collection is characterized by a different combination of $p_C$ and $p_C'$.

A multiplex set within a multiplex collection is defined as a multiplex collection member (primer library member). In other words, a multiplex set is a plurality of sets of primers for employment in a method of the invention, wherein the plurality is characterized in that each member set differs from any other member set in their combination of $p_C$ and $p_C'$, but for all member sets, $k_1$ and $k_1'$ (and, where applicable, $k_2$ and $k_2'$) are the same. The multiplex collection members can thus be used together, within the same multiplex PCR, and different multiplex collection members (discriminated by different K-boxes) will be used in repeated PCR/sequencing rounds.

To demonstrate the validity and power of the present invention, a PCR-based analysis of T-cell receptor beta (TCRβ) gene rearrangements was performed.

In general, the use of a two-step PCR strategy for TCR analyses has the advantage that the initial PCR with gene-specific TCR primers requires only a few PCR cycles minimizing PCR-generated bias, and thereafter the first amplificate is amplified evenly with the adaptor specific primers by a further PCR step. Furthermore, different adaptors suitable for different NGS platforms can be added by the second PCR.

In one embodiment, sequences for the target-binding tract of left ($p_C$) initial primer are those given as SEQ ID NO 001-045, and right ($p_C'$) initial primer sequences are those given as SEQ ID NO 046-058. In another embodiment for the target-binding tract of left ($p_C$) initial primer are those given as SEQ ID NO 189-232, and right ($p_C'$) initial primer sequences are those given as SEQ ID NO 233-246. The primers given as SEQ ID NO 001-058 and as SEQ ID NO 189-246 were optimized in two aspects: 1) to have a similar annealing temperature and 2) to minimize self priming.

The methods, sets of primers, collections and multiplex collections provided herein are of particular use in methods for analysing in vitro the TCRβ repertoire of a human patient.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

EXAMPLES

In the proof of principle experiments $k_1/k_1$' (with a lower case k) are together also termed $K_1$ with a capital letter and $k_2/k_2$' sequence tracts are thereafter also termed $K_2$. Furthermore, $s_1/s_1$' sequence tracts are thereafter also termed S. In general, the "prime" or apostrophe (') indicates that a sequence tract or element has a similar functional characteristic as its non-prime counterpart, but is located on a primer on the other side of the target sequence.

Example 1: Proof of Principle Experiments for $K_1$ Function

The basic experimental layout to demonstrate contamination suppression is outlined below:
1) PCR products of the first amplification were defined as a 100% contamination and were used as template for the second amplification. In order to demonstrate the function and effectiveness of $K_1$ sequence tracts to suppress this contamination, $K_1$ mismatches of different length (N=1, 2, 3, 4, 6 bp) between primers of the first and second PCR amplification were investigated. Furthermore, effects on contamination suppression, (i) employing polymerases with and without proofreading activity and (ii) primers with and without phosphorothioate bonds or LNAs were analysed.
2) For comparison and to simulate the situation without contamination suppression, simultaneous PCRs employing primers with completely matching $K_1$ sequences were performed.
3) The amount of the PCR products generated by the PCRs under (1) and (2) were quantified and normalized as described more detailed below. Replicates were performed for all experiments and the mean and standard deviation of PCR product quantity was calculated to obtain statistical reliable results.

If a reamplification with $K_1$ sequence tracts that mismatch between the first and the second amplification primers showed no PCR product after the second amplification, this was regarded as a complete suppression of the contamination from the primary amplification.

If a reamplification with $K_1$ sequence tracts that mismatch between the first and the second amplification primers showed PCR products after the second amplification, this was regarded as an incomplete suppression of the contamination from the primary amplification.

Detailed Description of the Methods:

PCR was performed using a DNA thermal cycler (PE 9700, Perkin Elmer, Rodgau, Germany). As template for first amplification reactions 100 ng DNA from the T-cell lymphoma cell line Peer was applied, which carries a known TCRβ gene rearrangement employing the V-4 and J-2-.1 segments.

Figure 1:
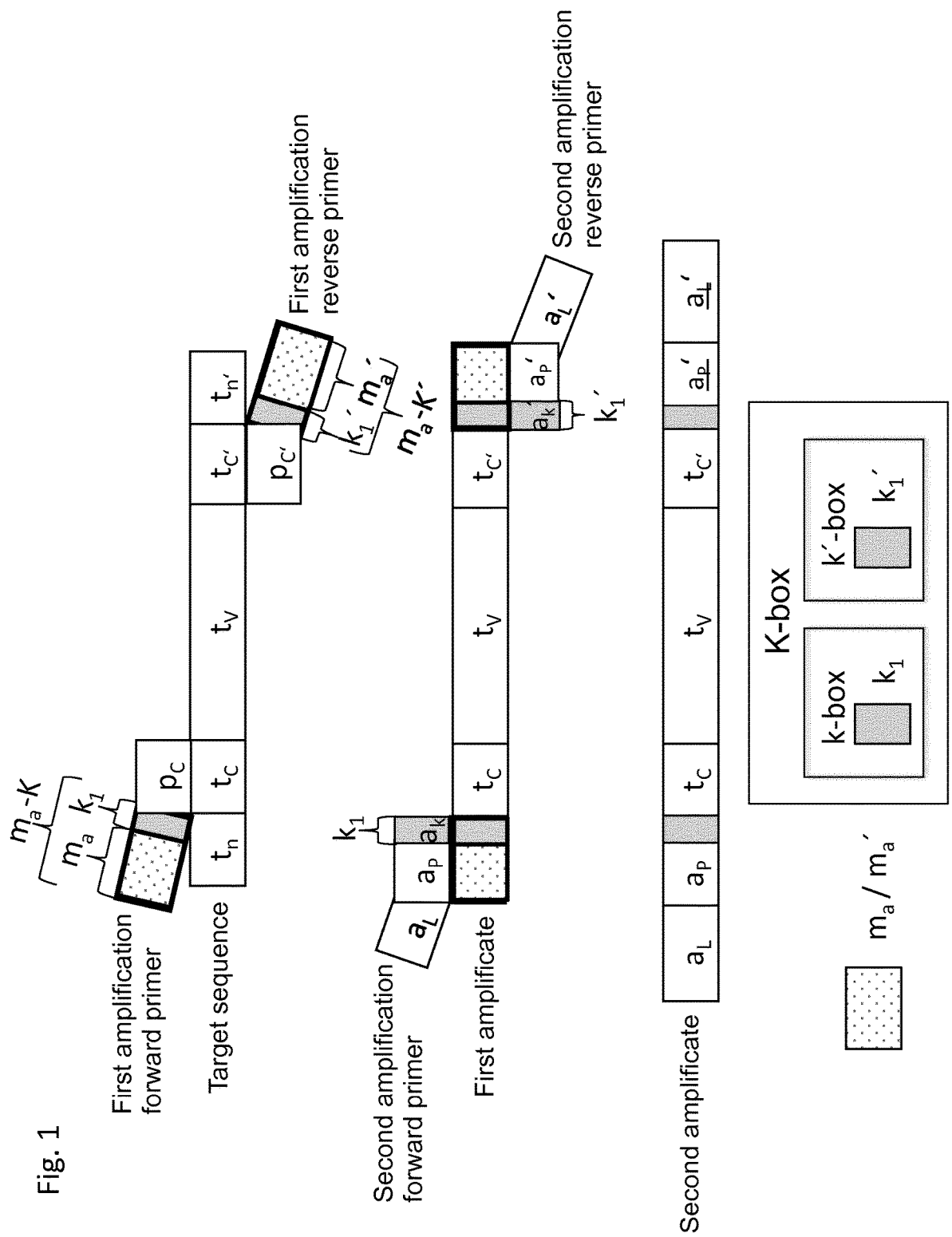
FIG. 1 shows the primers, target and first and second amplificate of the method of the invention, wherein the sequence tract comprises a sequence element $k_1$ and the sequence tract $m_a$-K' comprises a sequence element $k_1$'. Reverse complementary sequence tracts are underlined.

The initial primers used for the first round of amplification comprised in order from 5' to 3' end a sequence tract $m_a$-K and a sequence tract $p_C$ (FIG. 1). Sequence tract $p_C$ provided target specificity, while $m_a$-K provided a non-target-specific sequence tract, parts or all of which can be used for hybridization of a second "adaptor" primer. The left initial PCR primers had a sequence $m_a$-K-$p_C$ with the matching sequence $p_C$ to the V-4 segment (SEQ 183; TTATTCCTT-CACCTACACACCCTGC), whereas the right initial primers which had the sequence and $m_a$-K'-$p_C$' with the matching sequence $p_C$' (SEQ ID NO 184; AGCACTGTCAGCCGGGTGCCTGG) to the J-2.1 segment.

The 3' end of the k-box of forward initial primers had the sequence element S with the two nucleotides "GG", whereas the 3' end of the k'-box of the initial reverse primer had a sequence element s' with two nucleotides "TA".

Furthermore, the k-box of the forward initial primers had a sequence element $m_a$ (SEQ ID NO 185; CGCTCTTCC-GATCT) on the 5' end and the k'-box of the initial reverse primers had a sequence element $m_a$' (SEQ ID NO 186; TGCTCTTCCGATCT) on the 5' end (See FIG. 3 for the overview of the sequence tract names).

As listed in Table 2, the k-box of the initial forward primers harboured different $k_1$ and $k_2$ sequences and the k'-box of the initial reverse primers harboured different $k_1$' and $k_2$' sequences.

TABLE 2 k-box and k'-box element sequences are listed as present in 5'-3'orientation of the forward or reverse primers.

| k-box name | $k_1$ sequence | $k_2$ sequence | k'-box name | $k_1$' sequence | $k_2$' sequence |
|---|---|---|---|---|---|
| 1bpV1 | G | G | 1bJ1 | C | C |
| 1bpV2 | A | C | 1bpJ2 | T | G |
| 2bpV1 | AC | G | 2bpJ1 | TG | C |
| 2bpV2 | CA | C | 2bpJ2 | GT | G |
| 3bpV1 | ACC | G | 3bpJ1 | TGG | C |
| 3bpV2 | CAG | C | 3bpJ2 | GTC | G |

First amplification steps were performed in a final volume of 50 μl with final concentrations of 1×PCR Buffer containing 3 mM $MgCl_2$, 0.2 mM of each dNTP, 1.0 μM forward primer and 1.0 μM reverse primer and 1 unit AmpliTaq Gold DNA Polymerase (Applied Biosystems, Foster City, Calif., USA) and the following cycling conditions: 1 cycle at 95° C. for 15 min, 34 cycles at 95° C. for 30 s, 65° C. for 45 s and 72° C. for 45 sec respectively, and a final 10 min elongation step at 72° C. Primary PCR products were purified using the QIAquick PCR Purification Kit (Qiagen, Hilden, Germany) according to the manufacturer's instructions. DNA concentration was determined via the Qubit® 1.0 Fluorometer (Invitrogen, Darmstadt, Germany). As template for the second amplification 500 pg from the purified first amplification product was used.

For second amplification a pair of adaptor PCR primers comprising a left adaptor PCR primer having a sequence $a_L$-$a_P$-$a_K$ and a right adaptor PCR primer having a sequence $a_L'$-$a_P'$-$a_K'$ was employed.

The left adaptor primers had the sequence element $a_L$-$a_P$ (SEQ ID NO 187) whereas the right adaptor primers had the sequence element $a_L'$-$a_P'$ (SEQ ID NO 188).

Furthermore, the k-box of the forward adaptor primer harbored different $k_1$ sequences and the k'-box of the reverse adaptor primers harbored different $k_1'$ (listed in Table 2).

Since $K_1$ mismatches of the second amplification primer can be removed at the 3' end by the 3'-5' exonuclease-activity of a proofreading polymerase during the second amplification, the strength of a protective effect of phosphorothioates at (i) the first, (ii) the first and second (iii) and at the first to third position from the 3' end of the k-box and k'-box from the left (forward) and right (reverse) second amplification primer, respectively, was analysed in comparison to primers without protective phosphorothioate bonds.

The second amplification steps were performed (i) with a proofreading polymerase (Phusion High-Fidelity DNA Polymerase (Finnzymes, Espoo, Finland)) or (ii) a polymerase without proofreading activity (AmpliTaq Gold).

For PCRs with proofreading polymerase the second amplification step was performed in a final volume of 50 μl including final concentrations of 1× Phusion HF Buffer with 1.5 mM $MgCL_2$, 0.05 mM of each dNTP, 1.0 μM forward primer, 1.0 μM reverse primer and 1 unit Phusion High-Fidelity DNA Polymerase. The following thermal cycling conditions were used for the second amplification: 1 cycle at 98° C. for 30 s, 12 cycles at 98° C. for 10 s, 58° C. for 30 s and 72° C. for 30 s respectively, and a final 5 min elongation at 72° C.

For PCRs with AmpliTaq-Gold the second amplification step was performed in a final volume of 50 μl with final concentrations of 1×PCR Buffer, 3 mM $MgCl_2$, 0.2 mM of each dNTP, 1.0 μM forward primer and 1.0 μM reverse primer and 1 unit AmpliTaq Gold DNA Polymerase. The following thermal cycling conditions were used for the second amplification: 1 cycle at 95° C. for 15 min, 23 cycles at 98° C. for 10 s, 54° C. for 30 s and 72° C. for 30 s, respectively, and a final 5 min elongation step at 72° C.

PCR products were analysed on a 6% acrylamide gels and Tif files were produced with Biorad Geldoc 2000 (Munchen, Germany) using default conditions. PCR bands were further quantified with the FusionCapt Advance software (Vilber Lourmat, Eberhardzell, Germany). For quantification of the PCR products, equal areas (=gates) were analysed from (i) a gel quantification standard (=a Peer PCR product, 8 μl) which was set to 100% for each analysis, (ii) the PCR products (iii) a no template control (NTC) and (iv) the background gate. As FusionCapt Advance software parameters linear background subtraction was set for each gel in the middle of the background band and a rolling ball background subtraction (size=11) was employed. With the help of Microsoft Excel the mean and standard derivation (SDN) of replicated experiments was determined.

Results

The results for the experiments regarding the $K_1$-mediated suppression of contamination by mismatches in the K-boxes including the impact of the number of phosphorothioate bonds are given as single values in Table 3. A summary of Table 3 is given in Table 4. The second amplification primers in the experiments had 0-3 phosphorothioate bonds. A 100% contamination was simulated (a PCR product amplified with the Peer specific first amplification primers described above, employing Peer DNA as template) by adding a PCR product generated in a first PCR round into the second PCR. The second PCR was performed with matching second amplification primers ($K_1$=0 bp mismatch) and second amplification primers with 1 bp and 2 bp $K_1$ mismatches (summing up the $K_1$ mismatches of the forward and reverse primer).

The usage of mismatched K-boxes leads to a strong reduction of amplification, which was more pronounced when using 2 bases as compared to only one base. This demonstrates the validity our concept (Table 3 and 4).

TABLE 3

Effect of the number of $K_1$ mismatches (1 and 2 bp) on contamination suppression employing second amplification primers with 3, 2, 1 and 0 phosphorothioate (PT) bonds at their 3'end and proofreading polymerase. As gel quantification (quant) standard the same Peer TCR PCR product was used on each gel for normalization of the PCR product quantities and was set to 100%. Therefore, Vol. % larger than 100% can be achieved. Relevant for the effect of contamination suppression are the summary statistics (Table 4). (FA = first amplification, SA = second amplification, NTC no template control, bp = base pair, Vol. % volume percent as determined by FusionCapt Advance software, PT = phosphorothioate bond).

| Analysed sample/ FA primer combination | SA primer combination | $K_1$ mismatch (bp) | Vol. % (3 PT) | Vol. % (2 PT) | Vol. % (1 PT) | Vol. % (0 PT) |
|---|---|---|---|---|---|---|
| Gel quant standard | | | 100.0 | 100.0 | 100.0 | 100.0 |
| Peer 1bpV1 1bpJ1 | 1bpV1 1bpJ1 | 0 | 136.7 | 163.1 | 152.4 | 176.9 |
| Peer 1bpV1 1bpJ1 | 1bpV1 1bpJ2 | 1 | 28.7 | 38.4 | 63.6 | 171.8 |
| Peer 1bpV1 1bpJ1 | 1bpV2 1bpJ1 | 1 | 41.6 | 40.9 | 69.6 | 169.9 |
| Peer 1bpV1 1bpJ1 | 1bpV2 1bpJ2 | 2 | 17.0 | 12.2 | 28.7 | 127.7 |
| NTC 1bpV1 1bpJ1 | 1bpV1 1bpJ1 | 0 | 13.7 | 10.8 | 11.6 | 14.0 |
| Background | | | 12.0 | 9.7 | 8.8 | 15.7 |
| Gel quant standard | | | 100.0 | 100.0 | 100.0 | 100.0 |
| Peer 1bpV1 1bpJ2 | 1bpV1 1bpJ1 | 1 | 8.9 | 20.1 | 18.6 | 109.3 |
| Peer 1bpV1 1bpJ2 | 1bpV1 1bpJ2 | 0 | 84.8 | 119.5 | 100.5 | 122.0 |
| Peer 1bpV1 1bpJ2 | 1bpV2 1bpJ1 | 2 | 7.8 | 12.7 | 10.8 | 76.7 |
| Peer 1bpV1 1bpJ2 | 1bpV2 1bpJ1 | 1 | 13.9 | 22.0 | 25.8 | 104.3 |
| NTC 1bpV1 1bpJ2 | 1bpV1 1bpJ1 | 1 | 9.5 | 12.0 | 7.5 | 9.6 |
| Background | | | 7.7 | 11.0 | 8.0 | 7.9 |
| Gel quant standard | | | 100.0 | 100.0 | 100.0 | 100.0 |
| Peer 1bpV2 1bpJ1 | 1bpV1 1bpJ1 | 1 | 19.3 | 28.2 | 45.1 | 87.0 |
| Peer 1bpV2 1bpJ1 | 1bpV1 1bpJ2 | 2 | 10.6 | 11.9 | 14.2 | 80.5 |
| Peer 1bpV2 1bpJ1 | 1bpV2 1bpJ1 | 0 | 82.4 | 83.9 | 86.8 | 101.3 |

TABLE 3-continued

Effect of the number of $K_1$ mismatches (1 and 2 bp) on contamination suppression employing second amplification primers with 3, 2, 1 and 0 phosphorothioate (PT) bonds at their 3'end and proofreading polymerase. As gel quantification (quant) standard the same Peer TCR PCR product was used on each gel for normalization of the PCR product quantities and was set to 100%. Therefore, Vol. % larger than 100% can be achieved. Relevant for the effect of contamination suppression are the summary statistics (Table 4). (FA = first amplification, SA = second amplification, NTC no template control, bp = base pair, Vol. % volume percent as determined by FusionCapt Advance software, PT = phosphorothioate bond).

| Analysed sample/ FA primer combination | SA primer combination | $K_1$ mismatch (bp) | Vol. % (3 PT) | Vol. % (2 PT) | Vol. % (1 PT) | Vol. % (0 PT) |
|---|---|---|---|---|---|---|
| Peer 1bpV2 1bpJ1 | 1bpV2 1bpJ2 | 1 | 11.7 | 16.8 | 21.3 | 78.0 |
| NTC 1bpV2 1bpJ1 | 1bpV1 1bpJ1 | 1 | 9.2 | 8.5 | 8.9 | 7.8 |
| Background | | | 7.0 | 12.0 | 6.8 | 8.2 |
| Gel quant standard | | | 100.0 | 100.0 | 100.0 | 100.0 |
| Peer 1bpV2 1bpJ2 | 1bpV1 1bpJ1 | 2 | 10.1 | 10.2 | 11.8 | 81.7 |
| Peer 1bpV2 1bpJ2 | 1bpV1 1bpJ2 | 1 | 22.7 | 22.5 | 38.2 | 113.8 |
| Peer 1bpV2 1bpJ2 | 1bpV2 1bpJ1 | 1 | 11.4 | 11.3 | 13.1 | 103.0 |
| Peer 1bpV2 1bpJ2 | 1bpV2 1bpJ2 | 0 | 94.0 | 81.1 | 78.7 | 96.9 |
| NTC 1bpV2 1bpJ2 | 1bpV1 1bpJ1 | 2 | 9.3 | 8.2 | 8.1 | 10.0 |
| Background | | | 9.7 | 7.9 | 8.2 | 10.2 |

TABLE 4

Summary statistics of Table 3 (bp = base pair, Vol. % volume percent, SDN = standard deviation, PT = phosphorothioate bond). Quantities around 100% Vol. mean that there is no suppression of contamination. A lower Vol. % is the result of contamination suppression.

| $K_1$ mismatch (bp) | Vol. % (3 PT) Mean | Vol. % (3 PT) SDN | Vol. % (2 PT) Mean | Vol. % (2 PT) SDN | Vol. % (1 PT) Mean | Vol. % (1 PT) SDN | Vol. % (0 PT) Mean | Vol. % (0 PT) SDN |
|---|---|---|---|---|---|---|---|---|
| 0 | 99.5 | 21.9 | 111.9 | 33.2 | 104.6 | 28.7 | 124.3 | 31.8 |
| 1 | 19.8 | 10.3 | 25.0 | 9.6 | 36.9 | 19.7 | 117.1 | 32.9 |
| 2 | 11.4 | 3.4 | 11.8 | 0.9 | 16.4 | 7.2 | 91.7 | 20.9 |

The mean of all NTCs in Table 3 was 9.7 (SDN: 1.9) and the mean of background was 9.4 (SDN: 2.3).

Taken together, Table 3 and 4 demonstrate that in a setting with a proofreading polymerase employed in the second amplification, contamination suppression is much more effective with phosphorothioate bonds at the 3' end of the k-box and k'-box of reamplification primers. Furthermore, an increasing number of $K_1$ mismatches leads to improved contamination suppression. For example with 2 bp $K_1$ mismatches and 2 phophorothioate bonds the contamination (mean of 11.8, SDN: 0.9) is almost suppressed to NTC or background level.

Further experiments with longer $K_1$ mismatches revealed a complete suppression of contamination. The effectiveness of $K_1$ mismatches of 2, 3, 4, and 6 bp total length, to suppress contaminations was analysed in comparison to controls without $K_1$ mismatches. The second amplification primers in these experiments had 3 phosphorothioate bonds. The results are given in Table 5. A summary statistic with mean and standard deviation of the results in Table 5 is given in Table 6.

TABLE 5

Effect of the number of $K_1$ mismatches (2, 3 4 and 6 bp total length) on contamination suppression employing second amplification primers with 3 phosphorothioate bonds at their 3'end and proofreading polymerase. As gel quantification (quant) standard the same Peer TCR PCR product was used on each gel for normalization of the PCR product quantities and was set to 100%. Therefore, Vol. % larger than 100% can be achieved. Quantities around 100% Vol. mean that there is no contaminations suppression. A lower Vol. % is a result of contamination suppression. (FA = first amplification, SA = second amplification, NTC = no template control, bp = base pair, Vol. % volume percent, PT = phosphorothioate bond).

| Analysed sample/ FA primer combination | SA primer combination | Vol. % (3 PT) | $K_1$ mismatch (bp) |
|---|---|---|---|
| Gel quant standard | | 100.0 | |
| Peer 2bpV1 2bpJ1 | 2bpV1 2bpJ1 | 113.8 | 0 |
| Peer 2bpV1 2bpJ1 | 2bpV1 2bpJ2 | 11.5 | 2 |
| Peer 2bpV1 2bpJ1 | 2bpV2 2bpJ1 | 10.4 | 2 |
| Peer 2bpV1 2bpJ1 | 2bpV2 2bpJ2 | 10.9 | 4 |
| NTC 2bpV1 2bpJ1 | 2bpV1 2bpJ1 | 10.6 | 0 |
| Background | | 9.5 | |
| Gel quant standard | | 100.0 | |
| Peer 2bpV1 2bpJ2 | 2bpV1 2bpJ1 | 9.8 | 2 |
| Peer 2bpV1 2bpJ2 | 2bpV1 2bpJ2 | 99.3 | 0 |
| Peer 2bpV1 2bpJ2 | 2bpV2 2bpJ1 | 8.5 | 4 |
| Peer 2bpV1 2bpJ2 | 2bpV2 2bpJ2 | 8.9 | 2 |
| NTC 2bpV1 2bpJ2 | 2bpV1 2bpJ1 | 7.6 | 2 |
| Background | | 8.0 | |

TABLE 5-continued

Effect of the number of $K_1$ mismatches (2, 3 4 and 6 bp total length) on contamination suppression employing second amplification primers with 3 phosphorothioate bonds at their 3'end and proofreading polymerase. As gel quantification (quant) standard the same Peer TCR PCR product was used on each gel for normalization of the PCR product quantities and was set to 100%. Therefore, Vol. % larger than 100% can be achieved. Quantities around 100% Vol. mean that there is no contaminations suppression. A lower Vol. % is a result of contamination suppression. (FA = first amplification, SA = second amplification, NTC = no template control, bp = base pair, Vol. % volume percent, PT = phosphorothioate bond).

| Analysed sample/<br>FA primer combination | SA primer combination | Vol. % (3 PT) | $K_1$ mismatch (bp) |
|---|---|---|---|
| Gel quant standard | | 100.0 | |
| Peer 2bpV2 2bpJ1 | 2bpV1 2bpJ1 | 11.2 | 2 |
| Peer 2bpV2 2bpJ1 | 2bpV1 2bpJ2 | 8.1 | 4 |
| Peer 2bpV2 2bpJ1 | 2bpV2 2bpJ1 | 88.9 | 0 |
| Peer 2bpV2 2bpJ1 | 2bpV2 2bpJ2 | 8.5 | 2 |
| NTC 2bpV2 2bpJ1 | 2bpV1 2bpJ1 | 7.7 | 2 |
| Background | | 9.4 | |
| Gel quant standard | | 100.0 | |
| Peer 2bpV2 2bpJ2 | 2bpV1 2bpJ1 | 10.8 | 4 |
| Peer 2bpV2 2bpJ2 | 2bpV1 2bpJ2 | 13.1 | 2 |
| Peer 2bpV2 2bpJ2 | 2bpV2 2bpJ1 | 9.6 | 2 |
| Peer 2bpV2 2bpJ2 | 2bpV2 2bpJ2 | 98.5 | 0 |
| NTC 2bpV2 2bpJ2 | 2bpV1 2bpJ1 | 11.8 | 4 |
| Background | | 11.1 | |
| Gel quant standard | | 100.0 | |
| Peer 3bpV1 3bpJ1 | 3bpV1 3bpJ1 | 70.1 | 0 |
| Peer 3bpV1 3bpJ1 | 3bpV1 3bpJ2 | 12.1 | 3 |
| Peer 3bpV1 3bpJ1 | 3bpV2 3bpJ1 | 22.4 | 3 |
| Peer 3bpV1 3bpJ1 | 3bpV2 3bpJ2 | 12.8 | 6 |
| NTC 3bpV1 3bpJ1 | 3bpV1 3bPJ1 | 19.0 | 0 |
| Background | | 9.9 | |
| Gel quant standard | | 100.0 | |
| Peer 3bpV1 3bpJ2 | 3bpV1 3bpJ1 | 10.0 | 3 |
| Peer 3bpV1 3bpJ2 | 3bpV1 3bpJ2 | 79.8 | 0 |
| Peer 3bpV1 3bpJ2 | 3bpV2 3bpJ1 | 9.2 | 6 |
| Peer 3bpV1 3bpJ2 | 3bpV2 3bpJ2 | 17.5 | 3 |
| NTC 3bpV1 3bpJ2 | 3bpV1 3bpJ1 | 8.4 | 3 |
| Background | | 8.2 | |
| Gel quant standard | | 100.0 | |
| Peer 3bpV2 3bpJ1 | 3bpV1 3bpJ1 | 8.6 | 3 |
| Peer 3bpV2 3bpJ1 | 3bpV1 3bpJ2 | 7.0 | 6 |
| Peer 3bpV2 3bpJ1 | 3bpV2 3bpJ1 | 71.5 | 0 |
| Peer 3bpV2 3bpJ1 | 3bpV2 3bpJ2 | 7.6 | 3 |
| NTC 3bpV2 3bpJ1 | 3bpV1 3bpJ1 | 6.8 | 3 |
| Background | | 7.8 | |
| Gel quant standard | | 100.0 | |
| Peer 3bpV2 3bpJ2 | 3bpV1 3bpJ1 | 7.2 | 6 |
| Peer 3bpV2 3bpJ2 | 3bpV1 3bpJ2 | 7.4 | 3 |
| Peer 3bpV2 3bpJ2 | 3bpV2 3bpJ1 | 9.2 | 3 |
| Peer 3bpV2 3bpJ2 | 3bpV2 3bpJ2 | 61.4 | 0 |
| NTC 3bpV2 3bpJ2 | 3bpV1 3bpJ1 | 8.0 | 6 |
| Background | | 8.8 | |

TABLE 6

Summary statistics of Table 5. Quantities around 100% Vol. means that there is no contamination suppression. A lower Vol. % is a result of the contamination suppression. (bp = base pair, Vol. % volume percent, SDN = standard deviation).

| $K_1$ mismatch | Vol. % Mean | Vol. % SDN |
|---|---|---|
| 0 | 85.4 | 16.7 |
| 2 | 10.4 | 1.4 |
| 3 | 11.9 | 5.0 |
| 4 | 9.6 | 1.3 |
| 6 | 9.1 | 2.3 |

In Table 5 the mean of all NTCs was 10.0 (SDN: 3.7) and the mean of background was 9.1 (SDN: 1.0).

In summary, Table 5 and 6 show that in a setting with a proofreading polymerase employed in second amplification and 3 phosphorothioate bonds at the 3"end of the k-box and k'-box of the second amplification primers $K_1$ mismatches of 4 bp (mean 9.6, SDN 1.3) and 6 bp (mean 9.1, SDN 2.3) lead to complete suppression of contaminations comparable to NTCs and background.

In another experiment the effect of the number of $K_1$ mismatches (1 and 2 bp) on contamination suppression employing second amplification primers without phosphorothioate bonds and a polymerase without proofreading activity (AmpliTaq Gold) was analysed (Table 7). Summary statistics for Table 7 are provided in Table 8.

TABLE 7

Effect of the number of $K_1$ mismatches (1 and 2 bp total length) on contamination suppression employing second amplification primers without phosphorothioate bonds and a polymerase without proofreading activity. As gel quantification (quant) standard the same Peer TCR PCR product was used on each gel for normalization of the PCR product quantities and was set to 100%. Therefore, Vol. % larger than 100% can be achieved. Quantities around 100% Vol. mean that there is no contaminations suppression. A lower Vol. % is a result of contamination suppression. (FA = first amplification, SA = second amplification, bp = base pair, Vol. % volume percent)

| Analysed sample/FA primer combination | SA primer combination | Vol. % | $K_1$ mismatch |
|---|---|---|---|
| Gel quant standard | — | 100 | |
| Peer 1bpV1 1bpJ1 | 1bpV1 1bpJ1 | 155.7 | 0 |
| Peer 1bpV1 1bpJ1 | 1bpV2 1bpJ1 | 92.1 | 1 |
| Peer 1bpV1 1bpJ1 | 1bpV2 1bpJ2 | 54.9 | 2 |
| NTC 1bpV1 1bpJ1 | 1bpV1 1bpJ1 | 13.8 | 0 |
| NTC 1bpV1 1bpJ1 | 1bpV2 1bpJ1 | 14.2 | 1 |
| NTC 1bpV1 1bpJ1 | 1bpV2 1bpJ2 | 11.9 | 2 |
| Background | — | 13.2 | |
| Gel quant standard | — | 100 | |
| Peer 1bpV1 1bpJ2 | 1bpV1 1bpJ2 | 51.0 | 2 |
| Peer 1bpV1 1bpJ2 | 1bpV1 1bpJ2 | 115.0 | 0 |
| Peer 1bpV1 1bpJ2 | 1bpV2 1bpJ2 | 84.7 | 1 |
| NTC 1bpV1 1bpJ2 | 1bpV2 1bpJ1 | 10.3 | 2 |
| NTC 1bpV1 1bpJ2 | 1bpV1 1bpJ2 | 10.8 | 0 |
| NTC 1bpV1 1bpJ2 | 1bpV2 1bpJ2 | 9.4 | 1 |
| Background | — | 9.8 | |
| Gel quant standard | — | 100 | |
| Peer 1bpV2 1bpJ1 | 1bpV1 1bpJ1 | 104.6 | 1 |
| Peer 1bpV2 1bpJ1 | 1bpV2 1bpJ1 | 120.3 | 0 |
| Peer 1bpV2 1bpJ1 | 1bpV1 1bpJ2 | 77.8 | 2 |
| NTC 1bpV2 1bpJ1 | 1bpV1 1bpJ1 | 38.0 | 1 |
| NTC 1bpV2 1bpJ1 | 1bpV2 1bpJ1 | 30.2 | 0 |
| NTC 1bpV2 1bpJ1 | 1bpV1 1bpJ2 | 20.3 | 2 |
| Background | — | 14.5 | |
| Gel quant standard | — | 100 | |
| Peer 1bpV2 1bpJ2 | 1bpV1 1bpJ1 | 50.1 | 2 |
| Peer 1bpV2 1bpJ2 | 1bpV2 1bpJ1 | 62.7 | 1 |
| Peer 1bpV2 1bpJ2 | 1bpV2 1bpJ2 | 89.1 | 0 |
| NTC 1bpV2 1bpJ2 | 1bpV1 1bpJ1 | 12.5 | 2 |
| NTC 1bpV2 1bpJ2 | 1bpV2 1bpJ1 | 16.5 | 1 |
| NTC 1bpV2 1bpJ2 | 1bpV2 1bpJ2 | 15.0 | 0 |
| Background | — | 11.2 | |

TABLE 8

A summary statistics of Table 7 is provided. Quantities around 100% Vol. mean that there is no contamination suppression. A lower Vol. % is a result of contamination suppression. (bp = base pair, Vol. % volume percent, SDN = standard deviation).

| $K_1$ mismatches | Vol. % Mean | Vol. % SDN |
|---|---|---|
| 0 | 120.0 | 23.7 |
| 1 | 86.0 | 15.2 |
| 2 | 58.5 | 11.3 |

The mean of all NTCs in Table 7 was 16.9 (SDN: 8.0) and the mean of background was 12.2 (SDN: 1.8).

In summary, Table 7 and 8 show that also in a setting with a polymerase without proofreading activity and second amplification primers without phosphorothioate bonds at the 3' end of the k-box and k'-box contamination suppression increases with an increasing number of $K_1$ mismatches.

Contamination Suppression by $K_1$ Employing a TCRβ Multiplex-Collection

To demonstrate that $K_1$ is able to suppress contaminations employing a multiplex collection (referred to as TCRβ multiplex collection) with 44 TCRβ V segment specific primers ($p_C$, SEQ ID NO 189-232) and 14 TCRβ J segment specific primers ($p_C'$, SEQ ID NO 233-246) was used in the first PCR amplification. Each of these primers had a 5' S sequence of two nucleotides in length (For the SEQ ID NO 189-193, 195, 197, 198, 201-211, 213-221, 223-229, 231, 233-241 and 243-246 the S sequence was "GG", for the SEQ ID NO 194, 200 and 230, the S sequence was "TG", for the SEQ ID NO 196, 199, 212, 222, 242 the S sequence was "GT", for the SEQ ID NO 232 the S sequence was "TT". The orientation of these S sequences is in 5'-3' direction of the primer.

Furthermore, in this TCRβ multiplex collection the k-box of the forward initial primers had the tail sequence element $m_a$ (SEQ ID NO 247 GCTCTTCCGATCT) on their 5' end and the k'-box of the initial reverse primers had a sequence element $m_a'$ (SEQ ID NO 247; GCTCTTCCGATCT) on their 5' end.

Second amplification primers were employed (i) with 2 phosphorothioate bonds at their 3' end and in another experiment with (ii) an LNA at the second position from the 3' end. Three primer sets (Set 1-3) were used with the set specific $K_1$ and $K_2$ sequences given in Table 9.

TABLE 9 k-box and k'-box element sequences are listed as present in 5'-3' orientation of the forward or reverse primers.

| Name | $k_1$ sequence | $k_2$ sequence | $k_1'$ sequence | $k_2'$ sequence |
|---|---|---|---|---|
| Set1 | CACCCAA | GAC | GTTGGTT | CGT |
| Set2 | AGTTTTG | CGG | GGTCATG | TGG |
| Set3 | CTTTAGA | GTG | GCCATTT | TAA |

The first PCRs (with AmpliTaq-Gold) and second PCRs (with the proofreading Phusion High-Fidelity DNA Polymerase) were performed as described above, with 100 ng of tonsillar DNA as template. The PCR results were quantified with the FusionCapt Advance software as described above.

The performed PCR reactions (all nine $K_1$ match and mismatch combinations possible for Set 1-3) and the results are given in Table 10.

TABLE 10

Analysis of contamination suppression by $K_1$ employing a TCRβ multiplex-collection. As gel quantification (quant) standard the same Peer TCR PCR product was used on each gel for normalization of the PCR product quantities and was set to 100%. Therefore, Vol. % larger than 100% can be achieved. Quantities around 100% Vol. mean that there is no contaminations suppression. A lower Vol. % is a result of contamination suppression. (FA = first amplification, SA = second amplification, Vol. % volume percent, PT = phosphorothioate bonds; LNA = locked nucleic acid)

| Analysed sample/ FA primer set | SA primer set | Vol. % (PT) | Vol. % (LNA) | $K_1$ match/ mismatch |
|---|---|---|---|---|
| Gel quant standard | — | 100 | 100 | — |
| Set1 | Set 1 | 113.6 | 62.8 | match |
| Set1 | Set 2 | 29.5 | 28.6 | mismatch |
| Set1 | Set 3 | 28.8 | 34.3 | mismatch |
| NTC Set1 | NTC Set1 | 24.1 | 26.9 | match |
| NTC Set1 | NTC Set2 | 24.1 | 31.0 | mismatch |
| NTC Set1 | NTC Set2 | 22.1 | 31.3 | mismatch |
| Background | — | 25.5 | 34.0 | — |
| Gel quant standard | — | 100 | 100 | — |
| Set2 | Set2 | 83.5 | 102.1 | match |
| Set2 | Set1 | 25.1 | 21.7 | mismatch |
| Set2 | Set3 | 23.5 | 24.2 | mismatch |
| NTC Set2 | NTCSet2 | 21.0 | 19.0 | match |
| NTC Set2 | NTCSet1 | 23.9 | 20.4 | mismatch |
| NTC Set2 | NTCSet3 | 29.0 | 23.0 | mismatch |
| Background | — | 23.6 | 20.7 | — |
| Gel quant standard | — | 100 | 100 | — |
| Set3 | Set3 | 104.8 | 50.9 | match |
| Set3 | Set1 | 28.7 | 14.4 | mismatch |
| Set3 | Set2 | 23.8 | 18.1 | mismatch |
| NTCSet3 | NTCSet3 | 26.8 | 18.3 | match |
| NTCSet3 | NTCSet1 | 21.3 | 20.0 | mismatch |
| NTCSet3 | NTCSet2 | 22.0 | 17.1 | Mismatch |
| Background | — | 26.8 | 21.5 | — |

A summary statistics of Table 10 is provided in Table 11. These results show, that in a $K_1$ match situation the contamination is amplified, whereas in the $K_1$ mismatch situation the contamination is not amplified (being comparable to background, considering the SDN).

TABLE 11

Summary statistics of Table 10. Quantities around 100% Vol. mean that there is no contaminations suppression. A lower Vol. % is a result of the contamination suppression. (Vol. % volume percent, SDN = standard deviation, PT = phosphorothioate bonds; LNA = locked nucleic acid).

| | Vol. % Mean (PT) | Vol. % SDN (PT) | Vol. % Mean (LNA) | Vol. % SDN (LNA) |
|---|---|---|---|---|
| Match | 100.6 | 12.6 | 71.9 | 21.9 |
| Mismatch | 26.6 | 2.5 | 23.6 | 6.6 |
| NTC | 23.8 | 2.5 | 23.0 | 5.1 |
| Background | 25.3 | 1.3 | 25.4 | 6.1 |

Example 2: Proof of Principle for $k_2$ and $k_2'$ Function

Figure 2:
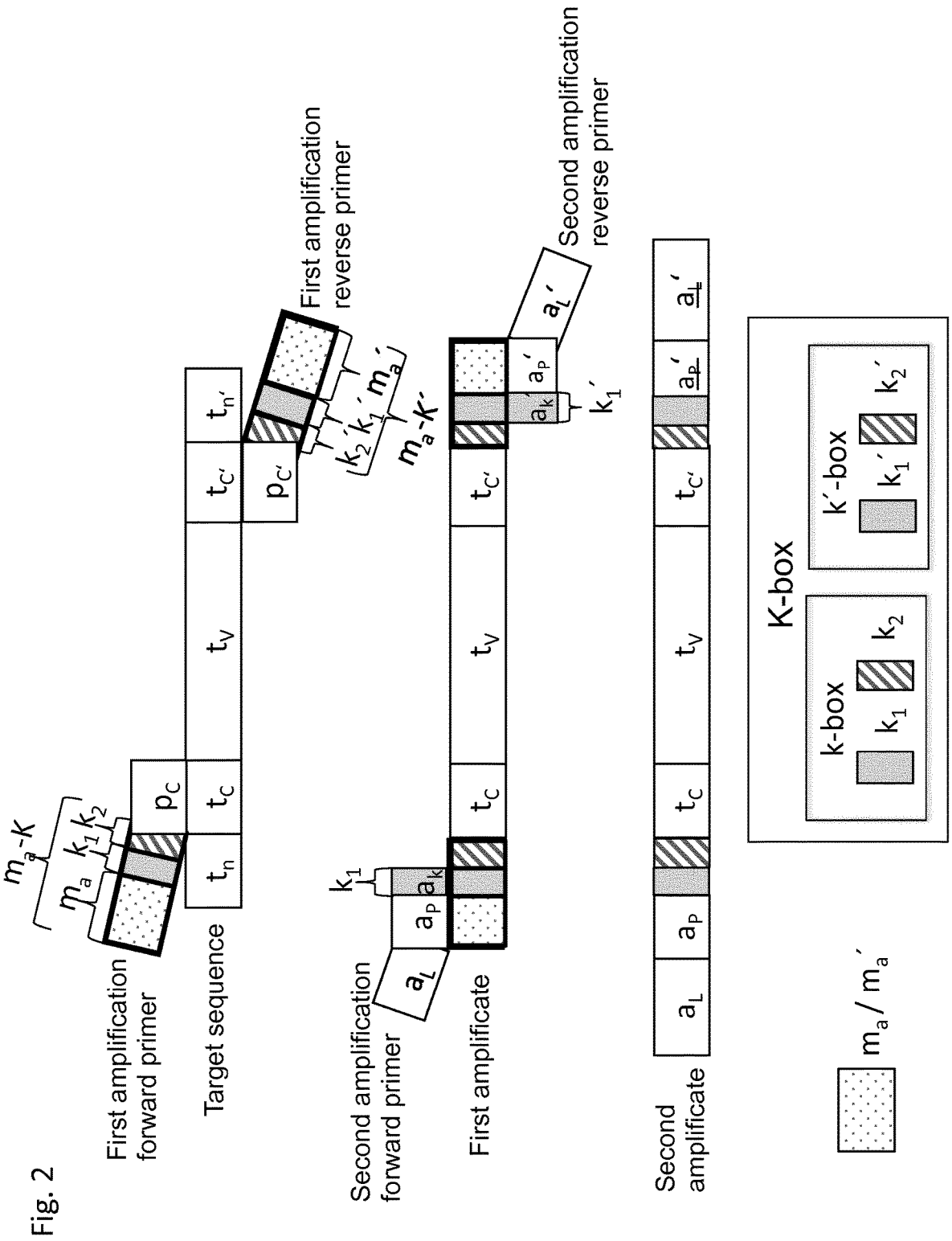
FIG. 2 shows the primers, target and first and second amplificate of the method of the invention, wherein the sequence tract $m_a$-K, in addition to $k_1$, comprises a sequence element $k_2$ and the sequence tract $m_a$-K', in addition to $k_1$', comprises a sequence element $k_2$'. Reverse complementary sequence tracts are underlined.
Figure 3:
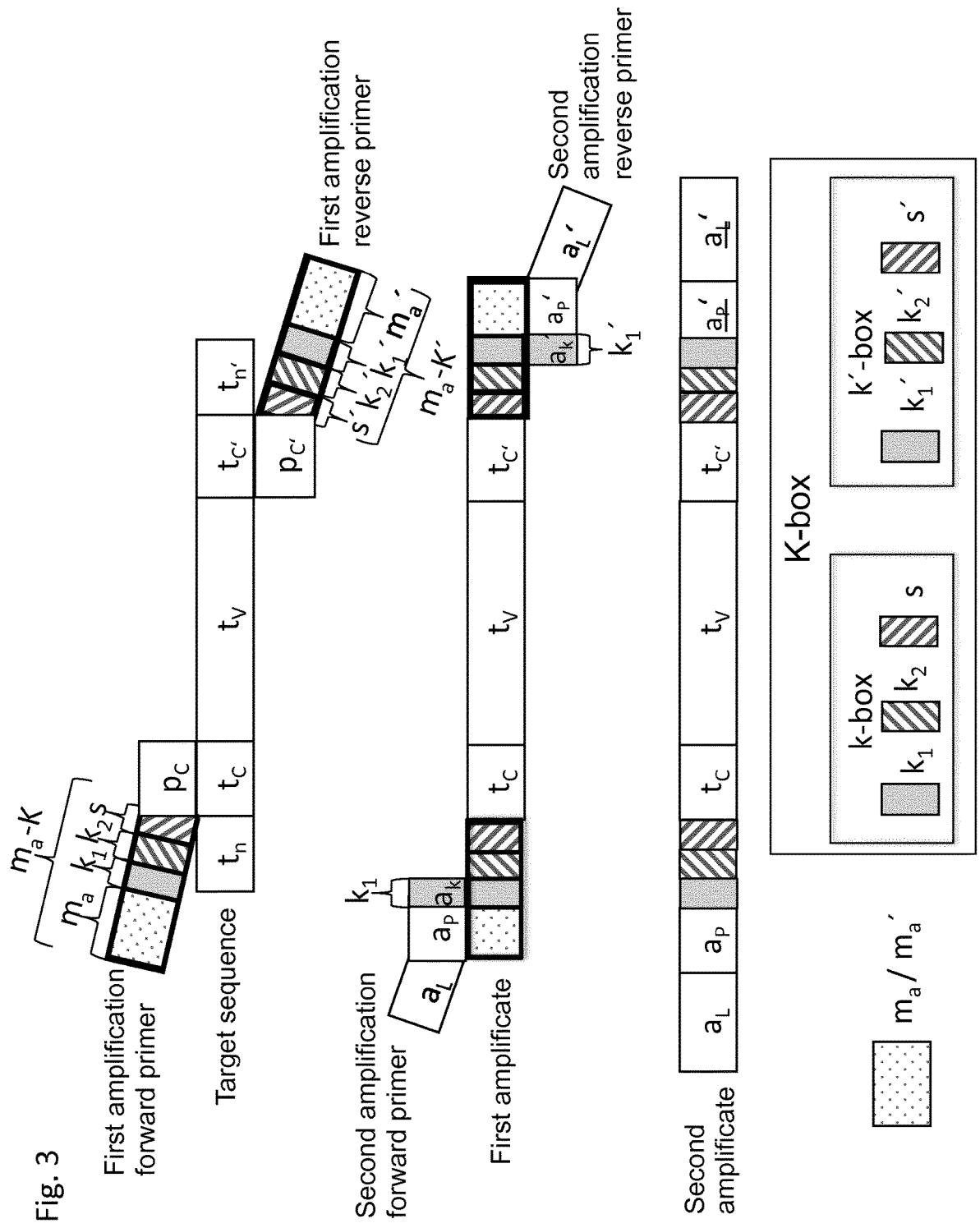
FIG. 3 shows the primers, target and first and second amplificate of the method of the invention, wherein the sequence tract $m_a$-K, in addition to $k_1$ and $k_2$ comprises a sequence element S and the sequence tract $m_a$-K', in addition to $k_1$' and $k_2$', comprises a sequence element s'. Reverse complementary sequence tracts are underlined.

As a short sequence element, $k_2$ is located at the 3'-end of the sequence element $k_1$ and $k_2'$ is a sequence element located at the 3'-end of the sequence element $k_1'$ (FIG. 2-3). $K_2$ serves to individualize the first primer pair of the set and have no complementary sequence elements on the second ("adaptor") primers. $K_2$ sequences are designed to detect contamination from previous amplification reactions and therefore control the suppression efficiency of $K_1$.

For this example, it is assumed that five samples are processed in parallel in a stripe with 5 PCR tubes for the first amplification and another stripe with 5 PCR tubes for the second amplification using five different primer sets. In this example for "Tube Nr. 1" one specific $k_2$ and/or $k_2$' sequence in the first amplification primer is employed as well as a $k_1$ and $k_1$' sequence matching the first and second amplification primer. In this setting a contamination can be clearly identified by a mismatched $k_2$ (or $k_2$') element if a "Tube Nr. 2" second amplification product contains $k_2/k_2$' elements of the "Tube Nr. 1" amplification product but $k_1$ and $k_1$' sequences of the "Tube Nr. 2" second amplification primers. In this case the contamination is caused by nonspecific priming of "Tube Nr. 2" $k_1$ and $k_1$' element of the second amplification primers to the "Tube Nr. 1" $k_1$ and $k_1$' element in the first amplification product. Furthermore the contamination amplification could be caused by partial or full degradation of the "Tube Nr. 2" $k_1$ and $k_1$' element by polymerases with proofreading activity. Since the $k_2/k_2$' elements are only present in the first amplification primers the contamination can still be identified in the second amplification product. Therefore, $k_2/k_2$' elements can be seen as a valuable safe lock mechanism to detect contaminations, complementing the already significant contribution of $k_1/k_1$' sequences to avoid such contaminations. There is a synergistic control function of $k_2/k_2$' that ensures the $k_1/k_1$' contamination suppression works 100%.

In order to demonstrate the function and effectiveness of $k_2/k_2$' sequence tracts to detect contaminations a first and second amplification with primers specific for the Peer TCR as described above were used with the following k-box and k'-box elements for the first forward amplification primer given in Table 2:

"Tube Nr. 1" (Set1) first amplification: forward primer 1bpV1 and reverse primer 1bpJ1

"Tube Nr. 2" (Set 2) second amplification: forward primer 1bpV2 and reverse primer 1bpJ1

Therefore, there is 1 bp $k_1$ mismatch between the "Tube Nr. 1" first amplification primer ($k_1$="G") and the "Tube Nr. 2" second amplification primer ($k_1$="A"). Furthermore, the "Tube Nr. 1" first amplification primer had the $k_2$="G" (Table 2).

The first "Tube Nr. 1" amplification was regarded to be a "100% contamination" ("Tube Nr. 1" primary amplification product) of "Tube Nr. 2" second amplification. Therefore, a second amplification was performed with "Tube Nr. 2" second amplification primers and the "Tube Nr. 1" first amplification product as template. In the gel analysis of the resulting second amplification PCR product there was a PCR product detectable, since due to the only 1 bp long $k_1$ mismatch this "Tube Nr. 1" contamination was not completely suppressed during second amplification (with "Tube Nr. 2" second amplification primers). This PCR product was sequenced.

Sanger sequencing of the amplicon identified the $k_2$ sequence of the amplicon as identifier of the "Tube Nr. 1" primary amplification forward primer ($k_2$="G"). Therefore, in this case the "Tube Nr. 1" specific $k_2$' sequence ($k_2$="G") identified the contamination from the "Tube Nr. 1" primary amplification product in the "Tube Nr. 2" second amplification (The "Tube Nr. 2" $k_2$ sequence would have been "C" for the "Tube Nr. 2" k-box 1bpV2 Table 2).

To gain a deeper understanding of this contamination detection and prevention system the second amplification in this experiment was performed independently with proofreading polymerase and with a polymerase without proofreading activity, with the PCR conditions described above for these reactions. As a result, in both experiments the contamination ("Tube Nr. 1" sample) could be identified by Sanger sequencing due to the contamination specific $k_2$ sequence ($k_2$="G").

The sequencing results revealed that with proofreading polymerase the $k_1$ sequence from the contaminating ("Tube Nr. 1") sample was found, whereas in the second amplification employing a polymerase without proofreading activity $k_1$ sequences from the second amplification primers ("Tube Nr. 2" amplification) were present. This is due to fact that there was a $k_1$ mismatch between the first and second amplification reverse primer and the $k_1$ element of the second amplification primer was removed (degraded) at the 3' end by the exonuclease-activity of a proofreading polymerase during the second amplification, despite the second amplification primers harbouring two phosphorothioate bonds. In contrast, the $k_1$ element of the second amplification primer was not removed using a polymerase without proofreading activity.

Taken together, the Sanger sequencing demonstrated the $k_2/k_2$' function to detect contamination. Thereby polymerase with or without proofreading polymerase can be used in second amplification. Importantly $k_2/k_2$' elements help to understand and control the function of $k_1/k_1$'. Another important result of this experiment is that if proofreading polymerase is employed, unexpected $k_1/k_1$' hybrids can be detected in the resulting sequence reads by bioinformatics methods and these sequences can be removed as contaminations.

Example 3: Proof of Principle for S Function

Figure 4:
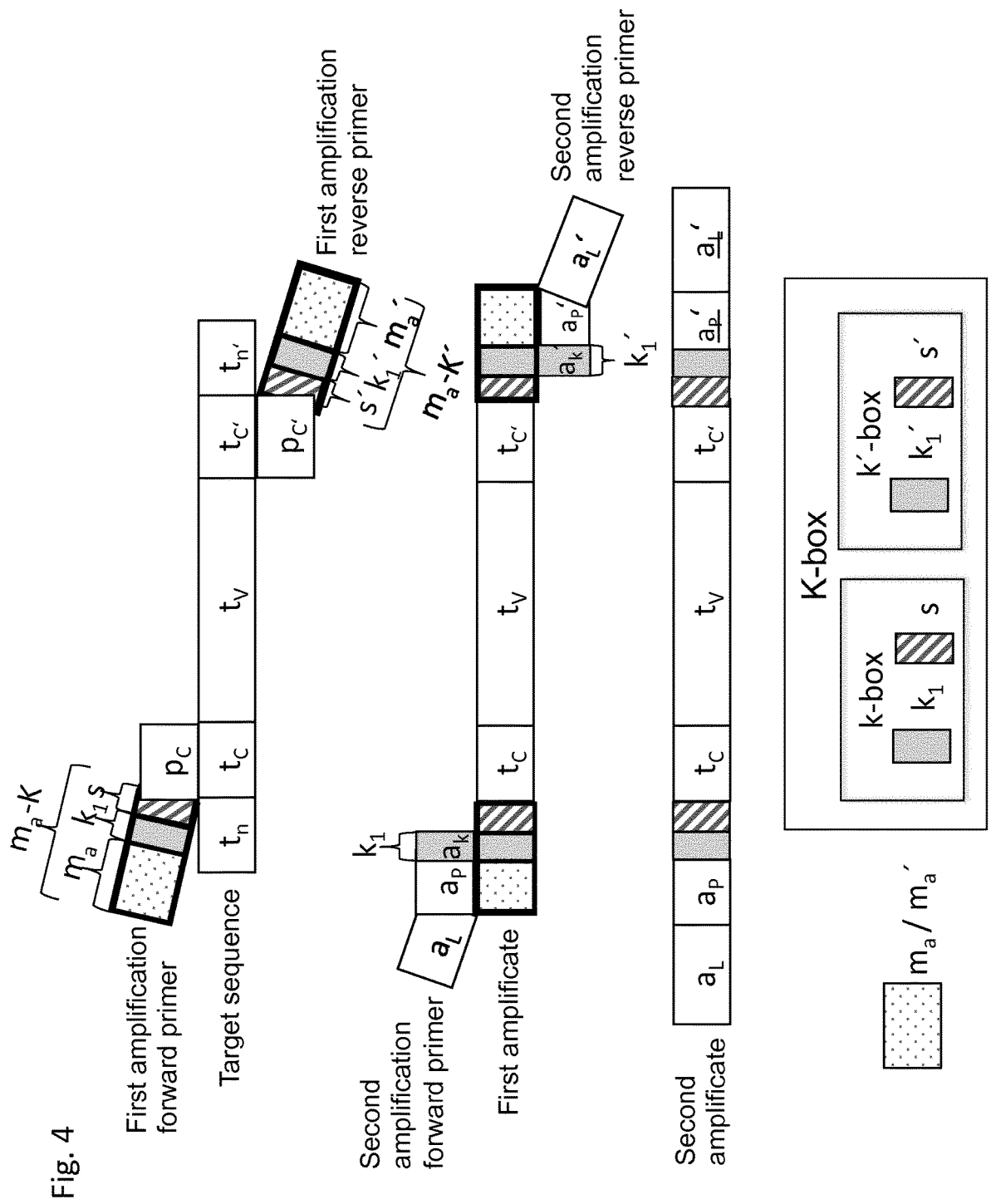
FIG. 4 shows the primers, target and first and second amplificate of the method of the invention, wherein the sequence tract $m_a$-K, in addition to $k_1$, comprises a sequence element S and the sequence tract $m_a$-K', in addition to $k_1$' comprises a sequence element s'. Reverse complementary sequence tracts are underlined.

A feature that improves on the performance of the above elements $k_1$ (and $k_1$') and $k_2$ (and $k_2$') is the introduction of short separator sequences s and s' (FIG. 3-4). S separates the constant initial primer sequence $p_C$ from the sequence tracts $k_1$ and $k_2$ and s' separates the constant initial primer sequence $p_C$' from $k_1$' and $k_2$' respectively. Since $k_1/k_1$' and $k_2/k_2$' vary among different primers used in subsequent reactions, it may well be that some variations of $k_1/k_1$' and/or $k_2/k_2$' coincidentally match in their last nucleotides on the 3' terminal end the sequence of the target next to the hybridizing part of the initial primer, $p_C$ or $p_C$'. Therefore, the target sequence-matching tract of the initial primer would be elongated, leading to higher annealing temperatures and thus, possibly, PCR bias.

As a proof of principle that S reduces PCR bias a simulation of an incidentally match of 6 bp length of the k-box and k'-box in the first amplification primers to the target sequence was analysed with S of 1, 2 and 3 bp length and no S sequence for comparison.

The first amplification was performed as described above with 100 ng template DNA from the T-cell lymphoma cell line Peer and the following cycle conditions. 1 cycle at 95° C. for 15 min, 29 cycles at 95° C. for 30 s, 68° C. for 45 s and 72° C. for 45 sec respectively, and a final 10 min elongation at 72° C.

The first amplification PCR primers had a sequence $m_a$K-$p_C$ with the matching sequence $p_C$ to the V-4 segment (SEQ ID NO 248; ACCTACACACCCTGC), whereas the right first amplification primers which had the sequence and $m_a$K'-$p_C$' had the matching sequence $p_C$' (SEC) ID NO 249; AGCCGGGTGCCTGG) to the J-2.1 segment. Furthermore, the k-box of the left first amplification primers had a sequence element $m_a$ (SEQ ID NO 250; CGCTCTTCC-GATCT) on the 5' terminus and the k'-box of the right first amplification primers had a sequence element $m_a$' (SEQ ID NO 251; TGCTCTTCCGATCT) on the 5' terminus.

An overview of the 6 bp matching K-box sequences to the V-4 segment and J-2.1 segment together with the s sequences of different length are given in Table 12.

TABLE 12

Overview of S sequences and 6 bp K-box sequences.

| Primer | K-box sequence | Template sequence match | S sequence |
|---|---|---|---|
| VKM | TCCTTC | Yes | none |
| VKMS1 | TTCCTT | Yes | G |
| VKMS2 | ATTCCT | Yes | GG |
| VKMS3 | TATTCC | Yes | AGG |
| VKMM | CAACGT | No | none |
| VKMMS1 | GGTTCA | No | G |

TABLE 12-continued

Overview of S sequences and 6 bp K-box sequences.

| Primer | K-box sequence | Template sequence match | S sequence |
|---|---|---|---|
| VKMMS2 | GGAGTA | No | GG |
| VKMMS3 | GCACTT | No | AGG |
| JKM | ACTGTC | yes | none |
| JKMS1 | CACTGT | yes | T |
| JKMS2 | GCACTG | yes | GT |
| JKMS3 | AGCACT | yes | CGT |
| JKMM | TGACGA | No | none |
| JKMMS1 | GTTGAC | No | T |
| JKMMS2 | ATGACT | No | GT |
| JKMMS3 | GTTGAG | No | CGT |

Some of the K-box sequences have a full-match to the V-4 segment and J-2.1 segment to simulate an incidentally matched K-box to the template sequence.
In the first column (Primer) the first letter "V" or "J" stands for the V- or J- TCR Primer in which the respective K-box is comprised,
"KM" stands for K-box match to template sequence;
"KMM" stand for K-box mismatch to template sequence and S1-3 gives the length of a separator sequence S (1-3 nucleotides).

TABLE 13

Experiment Nr. and results of proof of principle experiments to show that S can help to avoid a PCR bias by preventing K-box matches to the DNA template and therefore preventing unequal primer annealing temperatures and different amplification rates. Gel-St. (Gel quantification standard) = the same Peer TCR PCR product was used on each gel as standard for normalization of PCR product quantity and was set to 100%. Vol. % = volume percent, E1-5 = Experiment 1-5 (Replicates), SDN = standard deviation). In the third column (Primer) the primer pairs employed in the PCR are given. Thereby the first letter "V" or "J" stands for the V- or J-TCR Primer in which the respective K-box is comprised, "KM" stands for K-box match to template sequence; "KMM" stand for K-box mismatch to template sequence and S1-3 gives the length of a separator sequence S (1-3 nucleotides).

| Nr. | Sample | Primer | Vol. % E1 | Vol. % E2 | Vol. % E3 | Vol. % E4 | Vol. % E5 | Mean | SDN |
|---|---|---|---|---|---|---|---|---|---|
| 1 | Gel-St. | — | 100 | 100 | 100 | 100 | 100 | 100.0 | 0.0 |
| 2 | Peer | VKM JKM | 67.1 | 56.4 | 54.2 | 48.9 | 65.8 | 58.5 | 7.0 |
| 3 | Peer | VKMM JKMM | 27.6 | 13.6 | 15.1 | 14.9 | 16.7 | 17.6 | 5.1 |
| 4 | Peer | VKMS1 JKMS1 | 30.7 | 24.5 | 27.7 | 22.0 | 29.2 | 26.8 | 3.2 |
| 5 | Peer | VKMS2 JKMS2 | 39.8 | 20.5 | 19.5 | 26.6 | 14.9 | 24.3 | 8.6 |
| 6 | Peer | VKMS3 JKMS3 | 27.1 | 14.5 | 16.9 | 16.2 | 17.3 | 18.4 | 4.5 |
| 7 | Peer | VKMMS1 JKMMS1 | 16.6 | 11.4 | 14.6 | 13.4 | 13.7 | 13.9 | 1.7 |
| 8 | Peer | VKMMS2 JKMMS2 | 24.2 | 14.3 | 13.6 | 13.4 | 12.9 | 15.7 | 4.3 |
| 9 | Peer | VKMMS3 JKMMS3 | 21.0 | 9.6 | 21.3 | 14.4 | 21.4 | 17.5 | 4.8 |
| 10 | Background | — | 11.3 | 8.5 | 10.9 | 10 | 11.1 | 10.4 | 1.0 |
| 11 | Gel-St. | — | 100 | 100 | 100 | 100 | 100 | 100.0 | 0.0 |
| 12 | NTC | VKM JKM | 7.2 | 8 | 9.3 | 6.3 | 7.3 | 7.6 | 0.9 |
| 13 | NTC | VKMM JKMM | 9.5 | 7.8 | 9.4 | 6.8 | 6.9 | 8.1 | 1.1 |
| 14 | NTC | VKMS1 JKMS1 | 9.5 | 8.5 | 9.7 | 7.8 | 8.7 | 8.8 | 0.6 |
| 15 | NTC | VKMS2 JKMS2 | 9.2 | 9.1 | 10.8 | 6.8 | 7.7 | 8.7 | 1.3 |
| 16 | NTC | VKMS3 JKMS3 | 8.6 | 8.2 | 9.2 | 6.7 | 7.1 | 8.0 | 0.8 |
| 17 | NTC | VKMMS1 JKMMS1 | 9.1 | 9.1 | 9.7 | 6.9 | 7.9 | 8.5 | 0.9 |
| 18 | NTC | VKMMS2 JKMMS2 | 7.3 | 7.2 | 9.7 | 7.6 | 7.7 | 7.9 | 0.8 |
| 19 | NTC | VKMMS3 JKMMS3 | 7.7 | 9.1 | 9.5 | 6.7 | 7.7 | 8.1 | 0.9 |
| 20 | Background | — | 8 | 9.1 | 8.6 | 5.8 | 7.5 | 7.8 | 1.0 |

Table 13 shows that S sequences lead to a similar amplification despite of coincidentally template matching k-box and k'-box sequences. For example in Table 13 line 6 the amplification (Vol. %) with primers harbouring a S sequence of 3 bp length and template matching k-box and k'-box sequences have a mean of 18.4 (SDN 4.5) which is comparable to the amplification without template matching k-box and k'-box sequences in Table 13 line 3 with a mean of 17.6 (SDN 5.1).

This is the proof of the principle that S functions in a synergistic way to avoid PCR bias, due to altered primer annealing temperatures in the case of coincidentally template matching variations of some K-box sequences.

Example 4: Contamination Suppression by $K_1$ and Detection by $K_2$ Employing a TCRβ Multiplex Collection and NGS Analysis We employed the TCRβ multiplex collection (SEQ ID NO 189-246) with the related S sequences as described above, to analyse the effectiveness of $K_1$ to suppress contaminations and $K_2$ to detect residual contaminations. The $K_1$ and $K_2$ elements employed in Set 1-3 are described in Table 9).

Two analyses listed in Table 14 were performed in duplicates. In these experiments tonsillar DNA was used as template for the first amplification as well as the DNA of two T-cell lines (Jurkat and Karpas299). As template for the second amplification a total of 500 pg from the purified first amplification products was used as product mix.

In the first duplicate (Sample Nr. 1 and 2, Table 14) the first amplificate mix used as template for second amplification comprised 50% tonsillar amplificate (Set1), 25% Jurkat amplificate (Set1) and 25% Karpas299 amplificate (Set1). The second amplification primers were from Set1.

In the second duplicate (Sample 3 and 4, Table 14) the amplificate mix was used as template for second amplification comprised 50% tonsillar amplificate (Set1), 25% Jurkat amplificate (Set2) and 25% Karpas299 amplificate (Set3). The second amplification primers were from Set1.

Therefore In the first duplicate tonsillar TCRs were amplified without contamination protection and two spiked in contaminations (Jurkat, Karpas299 TCRs) and in the second duplicate tonsillar TCRs are amplified with contamination protection and the same spiked in contaminations (Jurkat, Karpas299).

TABLE 14

Experimental design to analyse contamination suppression by $K_1$ and detection by $K_2$ employing a TCRβ multiplex-collection and NGS analysis. For each of the 4 samples an individual standard Illumina barcodes was introduced into the amplification product by the right second amplification primer to allow NGS multiplexing.

| Sample Nr (Barcode) | Template for second amplification | Function |
|---|---|---|
| 1 | 50% First amplification with tonsillar DNA (Set 1) | Contamination with |
| 2 | 25% First amplification of Jurkat DNA (Set1) 25% First amplification of Karpas299 DNA (Set1) | Jurkat and Karpas 299 (no contamination protection) |
| 3 | 50% First amplification with tonsillar DNA (Set 1) | Contamination with |
| 4 | 25% First amplification of Jurkat DNA (Set2) 25% First amplification of Karpas299 DNA (Set3) | Jurkat and Karpas 299 (contamination protection) |

The resulting 4 NGS libraries were sequenced with MISEQ (Illumina) in the paired end modus (2×150 bp). By a tailored bioinformatics algorithm resulting reads were clustered and classified with respect to the K-box elements and the templates used. Frequencies of the respective tonsil and cell line reads and respective primer elements (Set 1-3) were counted and tabulated (Table 15).

The results given in Table 15 demonstrate that (i) without contamination protection (sample 1 and 2) the 2 cell line contaminations were detected with the expected percentage of approximately 25%. Strikingly in sample 3 and 4 due to the contamination protection by $K_1$ the 2 cell line contaminations were suppressed totally (cell line 1) and down to a percentage of 0.01 in (cell line 2). The residual cell line 2 contamination could be detected by $K_2$.

TABLE 15

NGS results of contamination suppression analysis described in Table 14. The Set information of the related reads refers always to the triplet (Tonsil/cell line 1/cell line 2).

| Sample | SET | Tonsil | Cell line 1 (Jurkat) | Cell line 2 (Karpas299) | Total read number |
|---|---|---|---|---|---|
| 1 | (1/1/1) | 48.79% | 23.70% | 27.51% | 180226 |
| 2 | (1/1/1) | 49.74% | 23.30% | 26.96% | 272669 |
| 3 | (1/2/3) | 99.99% | 0.00% | 0.01% | 314388 |
| 4 | (1/2/3) | 99.99% | 0.00% | 0.01% | 311956 |

Design of Suitable $k_1/k_1'$ and $k_2/k_2'$ Sequences.

To provide examples for suitable $k_1$ and $k_1'$ sequences, they were designed in a way to (a) optimally avoid cross-hybridization between all $k_1$ and $k_1'$ sequences given in one of the Tables 16-19 below, (b) adjust the melting temperatures of $k_1$ and $k_1'$ sequences in a narrow range and (c) to avoid low complex base compositions with >⅔ of the bases being the same nucleotide (A,C,G,T), Each of the Tables 16-19 consists of an equal number of $k_1$ and $k_1'$ sequences for the forward and reverse primers and a specific length (4, 5, r 6, 7 or 8 nucleotides).

In detail, features a)-c) were established by comparing all potential $k_1$ and $k_1'$ sequences of one specific length (4, 5, 6, 7 or 8 bp) against each other and excluded all those which were reverse-complements to any other $k_1$ and $k_1'$ sequences of this specific length. To further refine the $k_1$ and $k_1'$ sequences the design algorithm compared in a further step all $k_1$ and $k_1'$ sequences of one specific length (4, 5, 6, 7 or 8 bp) against all other reverse complement $k_1$ and $k_1'$ sequences of this specific length and excluded all $k_1$ and $k_1'$ sequences which either had >2 common bases at the 3' terminal end of the $k_1$ and $k_1'$ sequences or had >60% bases in common with another $k_1$ and $k_1'$ sequence.

The final results of this optimized $k_1$ and $k_1'$ sequences are given in Tables 16-19. It is understood that this are examples and that other optimized $K_1$-boxes with different selection criteria are possible.

Furthermore, examples of suitable $k_2/k_2'$ sequences are provided (Table 20), which were designed in a way to exclude all respective reverse complement sequences from the set of $k_2/k_2'$ sequences. As an example, if ATC is chosen as one possible $k_2$ element, GAT is automatically excluded from the set of $k_2'$ elements.

For final incorporation into the primer design, the K-boxes are designed as one unit being selected to form a minimum of cross-hybridization with the 3' ends of the primes employed.

TABLE 16

Optimized $k_1$ and $k_1'$ sequences of 4 bp length. For example the segment side A can be employed in the right primers and B in the left primers. Furthermore, the segment side B can be employed in the right primers and A in the left primers.

| Primer side | $k_1$ - or $k_1'$ sequence | Melting temperature |
|---|---|---|
| A | CTGA | 12 |
| A | AGTG | 12 |
| A | CAAC | 12 |
| A | GGAA | 12 |
| A | GTCA | 12 |
| A | AAGC | 12 |
| A | ATTA | 8 |
| A | AGCC | 14 |
| A | CGAG | 14 |
| A | AGGA | 12 |
| A | TAGA | 10 |
| B | GCGA | 14 |
| B | ACGG | 14 |
| B | CGTA | 12 |
| B | ACTC | 12 |
| B | CTTC | 12 |
| B | ACCA | 12 |
| B | GCAC | 14 |
| B | GACC | 14 |
| B | ATAC | 10 |
| B | CGGC | 16 |
| B | GATA | 10 |

TABLE 17

Optimized $k_1$ and $k_1'$ sequences of 5 bp length. For example the segment side A can be employed in the right primers and B in the left primers. Furthermore, the segment side B can be employed in the right primers and A in the left primers.

| Primer side | $k_1$ - or $k_1'$ sequence | Melting temperature |
|---|---|---|
| A | CTCTA | 14 |
| A | ATCAG | 14 |
| A | ATTGG | 14 |
| A | ATACG | 14 |
| A | ACGCA | 16 |
| A | ACCAA | 14 |
| A | AATGC | 14 |
| A | AAGGA | 14 |
| A | TCACA | 14 |
| A | ATATA | 10 |
| A | ATGTC | 14 |
| A | AGCTG | 16 |
| A | CAACC | 16 |
| B | GTTTA | 12 |
| B | GCTCC | 18 |
| B | CTTAA | 12 |
| B | GAGGC | 18 |
| B | ACACT | 14 |
| B | AATCG | 14 |
| B | CATCA | 14 |
| B | GTAGA | 14 |
| B | CTTTC | 14 |
| B | AAGCC | 16 |
| B | AAAGT | 12 |
| B | CGGAA | 16 |
| B | CTCAC | 16 |
| B | CGGAA | 16 |
| B | CTCAC | 16 |

TABLE 18

Optimized $k_1$ and $k_1'$ sequence of 6 bp length. For example the segment side A can be employed in the right primers and B in the left primers. Furthermore, the segment side B can be employed in the right primers and A in the left primers.

| Primer side | $k_1$ - or $k_1'$ sequence | Melting temperature [° C.] |
|---|---|---|
| A | CTCTGA | 18 |
| A | GGTTAA | 16 |
| A | GCCTTA | 18 |
| A | CGGACG | 22 |

TABLE 18-continued

Optimized $k_1$ and $k_1'$ sequence of 6 bp length. For example the segment side A can be employed in the right primers and B in the left primers. Furthermore, the segment side B can be employed in the right primers and A in the left primers.

| Primer side | $k_1$ - or $k_1'$ sequence | Melting temperature [° C.] |
|---|---|---|
| A | GTCAAA | 16 |
| A | GATCGA | 18 |
| A | CTTGTA | 16 |
| A | AACTTG | 16 |
| A | AATCAT | 14 |
| A | ACTATG | 16 |
| A | GCAACA | 18 |
| A | CGAAGC | 20 |
| A | GAGTCC | 20 |
| A | GGCAAC | 20 |
| A | AAATGT | 14 |
| A | CTATCA | 16 |
| B | AAGCTG | 18 |
| B | GCCCAA | 20 |
| B | ATCAGA | 16 |
| B | ACTCAG | 18 |
| B | GGTATA | 16 |
| B | AAAGGG | 18 |
| B | AATGCT | 16 |
| B | CCAAGG | 20 |
| B | ACGCGG | 22 |
| B | GACGGA | 20 |
| B | GCGCAC | 22 |
| B | GTAGAA | 16 |
| B | ACCGCA | 20 |
| B | AAACCC | 18 |
| B | AGAACT | 16 |
| B | GAGCTA | 18 |

TABLE 19

Optimized $k_1$ and $k_1'$ sequence of 7 and 8 nucleotide (nt) length. For example the segment side A can be employed in the right primers and B in the left primers. Furthermore, the segment side B can be employed in the right primers and A in the left primers.

| K1 "A 7 nt" | K1 "B 7 nt" | K1 "A 8 nt" | K1 "B 8 nt" |
|---|---|---|---|
| AACCAAC | GAGCACA | CGTGTCGC | AGGCACCA |
| CATGACC | CACCCAA | ATGATGAC | GCTTCTTA |
| CATGACC | CACCCAA | ATGATGAC | GCTTCTTA |
| AAATGGC | CTTCCTA | AAACCTGT | ATACTTCG |
| AGGTAGC | AGTTTTG | GAATGATA | ACGATTGG |
| TATGTCA | CTGTTAA | ATCGGTGC | GGCAGCGA |
| CTATGTA | CTTTAGA | GATGTTCA | ATGTTCGG |
| CATTGCG | AAGACGG | CTGCGACA | GGTGGCTA |
| AGAAGGA | AGCGGCC | CATCTAGA | CAATACCC |
| GATCTCC | CAGTAGG | AACGCTGA | CTATTTAC |
| ACTATGC | AGTGCCA | ATGCTGTG | TGCGAAAA |
| GACGCAC | GAGCACA | GAACACAA | CAAGCGAG |
| ACTTGAA | GAGCACA | CTTAAGTC | CAGCCGAA |
| CGGTGAC | CACCCAA | GAGAAGGC | CCCAAAAC |
| GAACTGA | AGTTTTG | GGATGTAA | AGGCACCA |
| CGGATTA | AGTTTTG | AGCAAGGA | AGGCACCA |
| GTATAAA | CTGTTAA | ACTCAGTA | GCTTCTTA |

TABLE 20

Examples for $k_2$ and $k_2'$ sequence of 3 bp length. For example the segment side A can be employed in the right primers and B in the left primers. Furthermore, the segment side B can be employed in the right primers and A in the left primers.

| Primer side | $k_2$ - or $k_2'$ sequence | Primer side | $k_2$ - or $k_2'$ sequence |
|---|---|---|---|
| A | ACG | B | GAC |
| A | CCA | B | CGG |
| A | TTA | B | GTG |
| A | TCG | B | TGT |
| A | GGT | B | AAG |

The invention claimed is:

1. A method for reducing cross-contamination between a plurality of nucleic acid amplification reactions for amplifying a target nucleic acid sequence $t_C$-$t_V$-$t_C'$ comprised within a sequence tract $t_n$-$t_C$-$t_V$-$t_C'$-$t_n'$, said method comprising conducting a plurality of amplification reactions, each reaction comprising a first amplification step, whereby said target nucleic acid sequence is amplified using
a left (forward) initial PCR primer having a sequence $m_a$-K-$p_C$ and
a right (reverse) initial primer having a sequence and $m_a$-K'-$p_C'$,
yielding a first amplificate,
wherein the sequences of K and K' are different in each reaction within the plurality of amplification reactions; and a second amplification step, whereby said first amplificate is amplified using
a left (forward) adaptor PCR primer having a sequence $a_L$-$a_P$-$a_K$ and
a right (reverse) adaptor PCR primer having a sequence $a_L'$-$a_P'$-$a_{K'}'$,
yielding a second amplificate only if $a_K$ will hybridize to K, and $a_{K'}$ will hybridize to K', and thereby reducing cross-contamination between each reaction within the plurality of reactions,
wherein the primer pairs used in the first and second amplification steps of each reaction within the plurality of reactions are different from the primer pairs used in every other reaction within the plurality of reactions, wherein $t_V$ is a variable region within said target nucleic acid sequence, $p_C$ is the same sequence as sequence element $t_C$ and $p_C'$ is the reverse complementary sequence to $t_C'$, K comprises a sequence element $k_1$ and a 3'-terminal sequence element s, and K' comprises a sequence element $k_1'$ and a 3'-terminal sequence element s', wherein $k_1$ and $k_1'$ each independently from one another are a sequence 2 to 9 nucleotides in length, s and s' are mismatch sequences selected not to form a continuous hybrid sequence with sequence element $t_n$ and $t_n'$, and s and s' are each independently 1, 2, 3, 4 or 5 nucleotides in length, and wherein in each amplification reaction of the plurality of reactions, $k_1$ and/or $k_1'$ is different from $k_1$ and/or $k_1'$ in every other amplification reaction within the plurality of reactions, $a_K$ is the same sequence as sequence element $k_1$ and $a_K'$ is the same sequence as sequence element $k_1'$, $a_P$-$a_K$ hybridizes to a contiguous sequence on $m_a$-K and $a_P'$-$a_K'$ hybridizes to a contiguous sequence on $m_a$-K', $p_C$, $p_C'$, $m_a$-K and $m_a$-K' each independently from one another are a sequence 10 to 40 nucleotides in length, and $a_L$ and $a_L'$ independently from one another can be any sequence.

2. The method according to claim 1, wherein K comprises a 3'-terminal sequence $k_1$-$k_2$-s, and K' comprises a 3'-terminal sequence $k_1'$-$k_2'$-s', wherein $k_2$ and $k_2'$ each independently from one another are a sequence 2 to 7 nucleotides in length, $a_K$ and $a_K'$ are selected not to hybridize to $k_2$ and $k_2'$, respectively;

for each left and right initial primers, one of $k_2$ and $k_2'$ are different from of any other $k_2$ and $k_2'$, respectively and $k_1$, $k_1'$, s and s' have the meaning outlined above.

3. The method according to claim 1, wherein $k_1$ and $k_1'$ each independently from one another are a sequence 5 to 9 nucleotides in length, s and s' are each independently 2, 3, or 4 nucleotides in length, and/or $k_2$ and $k_2'$ each independently from one another are a sequence 2 to 6 nucleotides in length.

4. The method according to claim 1, wherein for each left and right initial primers, each $k_1$ is different from of any other $k_1$ and each $k_1'$ is different from any other $k_1'$, and/or each $k_2$ is different from of any other $k_2$ and each $k_2'$ is different from any other $k_2'$.

5. The method according to claim 1, wherein $k_1$ and $k_1'$ and/or $k_2$ and $k_2'$ are selected not to hybridize to the sequence elements $t_n$ and $t_n'$.

6. The method according to claim 1, wherein said initial and adaptor primers comprise a left (forward) initial primer comprising a sequence element $p_C$ set forth herein as SEQ ID NO 002 and a right (reverse) initial primer comprising a sequence element $p_C'$ set forth herein as SEQ ID NO 047; or a left (forward) initial primer comprising a sequence element $p_C$ set forth herein as SEQ ID NO 189 and a right (reverse) initial primer comprising a sequence element $p_C'$ set forth herein as SEQ ID NO 235; and a left (forward) initial primer comprising a sequence element $m_a$ set forth herein as SEQ ID NO 083 and a right (reverse) initial primer comprising a sequence element $m_a$ set forth herein as SEQ ID NO 115; and a left (forward) adaptor primer comprising a sequence element $a_L$-$a_P$ set forth herein as SEQ ID NO 118 and a right (reverse) adaptor primer comprising a sequence element $m_a$ set forth herein as SEQ ID NO 150.

7. The method according to claim 1, wherein said left initial primer, said right initial primer, said left adaptor primer and/or said right adaptor primer are characterized by a nuclease resistant nucleotide or a nuclease resistant nucleotide analogue, or a nuclease resistant internucleosidic bond, on or near the 3' terminus of said primer.

8. The method according to claim 1, wherein in the first and/or second amplification step, a DNA polymerase having a 3'-5' exonuclease (proofreading) activity is used.

9. A method for sequencing a target sequence $t_C$-$t_V$-$t_C'$ comprised within a sequence tract $t_n$-$t_C$-$t_V$-$t_C'$-$t_n'$, comprising the steps of a) amplifying said target sequence by a method according to claim 1, b) sequencing said second amplificate including sequence elements $m_a$-K and/or $m_a$-K', yielding a set of readout sequences.

10. The method of claim 9, further comprising the steps of c) aligning each member of said set of readout sequences to sequence element $m_a$-K and/or $m_a$-K' comprised in said initial primer, respectively, and d) assigning a value of 0 or 1 as a measure of contamination to each sequence of said set of readout sequences, wherein complete alignment of a member of said set of readout sequences to said sequence element $m_a$-K or $m_a$-K' corresponds to a value of 0, and incomplete alignment of a member of said set of readout sequences to said sequence element $m_a$-K or $m_a$-K' corresponds to a value of 1; and (i) determining a percentage of contamination by adding all values assigned in step d), resulting in a value sum, and dividing said value sum by the total number of reads; and/or (ii) removing the sequences having a value of 1 from the sequence set.

* * * * *

SEQUENCE LISTING

<160> NUMBER OF SEQ ID NOS: 251

<210> SEQ ID NO 1
<211> LENGTH: 28
<212> TYPE: DNA
<213> ORGANISM: Artificial Sequence
<220> FEATURE:

```
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 1
aatttcactc tgaagatccg gtccacaa                                    28

<210> SEQ ID NO 2
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 2
cacttaaatc ttcacatcaa ttccctgg                                    28

<210> SEQ ID NO 3
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 3
ttaaaccttc acctacacgc cctgc                                       25

<210> SEQ ID NO 4
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 4
ttattccttc acctacacac cctgc                                       25

<210> SEQ ID NO 5
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 5
aactctgaga tgaatgtgag caccttg                                     27

<210> SEQ ID NO 6
<211> LENGTH: 27
<212> TYPE: DNA
<213> ORGANISM: Artificial Sequence
```

```
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 6
tgctctgaga tgaatgtgag tgccttg                                              27

<210> SEQ ID NO 7
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 7
agctctgagc tgaatgtgaa cgccttg                                              27

<210> SEQ ID NO 8
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for PCR"
      /organism="Artificial Sequence"

<400> SEQUENCE: 8
tcgctcaggc tggagtcggc tg                                                   22

<210> SEQ ID NO 9
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 9
attttcctgg ggttggagtc ggctg                                                25

<210> SEQ ID NO 10
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 10
ttccccctca cgttggcgtc tgctg                                                25

<210> SEQ ID NO 11
<211> LENGTH: 22
<212> TYPE: DNA
```

```
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for PCR"
      /organism="Artificial Sequence"

<400> SEQUENCE: 11
ccgctcaggc tgctgtcggc tg                                              22

<210> SEQ ID NO 12
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 12
ttcccgctca ggctggagtt ggctg                                           25

<210> SEQ ID NO 13
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 13 ttcccectca agctggagtc agctg                                           25

<210> SEQ ID NO 14
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 14
ttcccactca ggctggtgtc ggctg                                           25

<210> SEQ ID NO 15
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 15
ttcccgctca ggctggagtc agctg                                           25

<210> SEQ ID NO 16
<211> LENGTH: 25
```

```
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 16
tccactctga agttccagcg cacac                                      25

<210> SEQ ID NO 17
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 17
tccactctga cgatccagcg cacac                                      25

<210> SEQ ID NO 18
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 18
tctactctga agatccagcg cacag                                      25

<210> SEQ ID NO 19
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 19
tccactctga agatccagcg cacag                                      25

<210> SEQ ID NO 20
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 20
tccactctga cgatccagcg cacag                                      25

<210> SEQ ID NO 21
```

```
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 21
tccactctga cgattcagcg cacag                                25

<210> SEQ ID NO 22
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 22
tccactctga agatccagcg cacac                                25

<210> SEQ ID NO 23
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 23
tccaccttgg agatccagcg cacag                                25

<210> SEQ ID NO 24
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 24
cactctgaac taaacctgag ctctctg                              27

<210> SEQ ID NO 25
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 25 ctcccccctca ctctggagtc tgctg                               25
```

```
<210> SEQ ID NO 26
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 26 ttcccccctca ctctggagtc agcta                                25

<210> SEQ ID NO 27
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 27
ttcctcctca ctctggagtc cgcta                                 25

<210> SEQ ID NO 28
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 28
tccactctca agatccagcc tgcag                                 25

<210> SEQ ID NO 29
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 29
tccactctca agatccagcc tgcaa                                 25

<210> SEQ ID NO 30
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 30
tccactctga agatccagcc ctcag                                 25
```

```
<210> SEQ ID NO 31
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 31
cattctgaac tgaacatgag ctccttgg                                28

<210> SEQ ID NO 32
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 32
tctactctga aggtgcagcc tgcag                                   25

<210> SEQ ID NO 33
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 33
aacttccaat ccaggaggcc gaaca                                   25

<210> SEQ ID NO 34
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 34
tgtagccttg agatccaggc tacga                                   25

<210> SEQ ID NO 35
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 35
tcttccacgc tgaagatcca tcccg                                   25
```

<210> SEQ ID NO 36
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 36
agcatcctga ggatccagca ggtag                                     25

<210> SEQ ID NO 37
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 37
tttcctctca ctgtgacatc ggccc                                     25

<210> SEQ ID NO 38
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 38
ttgtccactc tgacagtgac cagtg                                     25

<210> SEQ ID NO 39
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 39
tgcagcctgg caatcctgtc ctcag                                     25

<210> SEQ ID NO 40
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 40
ttctccctgt ccctagagtc tgccat         26

<210> SEQ ID NO 41
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 41 tttccccctga ccctggagtc tgcca          25

<210> SEQ ID NO 42
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 42
ttccccctga tcctggagtc gccca           25

<210> SEQ ID NO 43
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 43
ttctccctga ttctggagtc cgcca           25

<210> SEQ ID NO 44
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 44
acattctcaa ctctgactgt gagcaaca        28

<210> SEQ ID NO 45
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 45

```
cggcagttca tcctgagttc taagaagc                                              28
```

<210> SEQ ID NO 46
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 46

```
ttacctacaa ctgtgagtct ggtgcc                                                26
```

<210> SEQ ID NO 47
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 47

```
cctacaacgg ttaacctggt ccccg                                                 25
```

<210> SEQ ID NO 48
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 48

```
cctacaacag tgagccaact tccct                                                 25
```

<210> SEQ ID NO 49
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 49

```
cccaagacag agagctgggt tccact                                                26
```

<210> SEQ ID NO 50
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

```
<400> SEQUENCE: 50
ttacctagga tggagagtcg agtcc                                          25

<210> SEQ ID NO 51
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 51
cctgtcacag tgagcctggt cccgt                                          25

<210> SEQ ID NO 52
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 52
cctagcacgg tgagccgtgt ccc                                            23

<210> SEQ ID NO 53
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 53
ttacccagta cggtcagcct agagc                                          25

<210> SEQ ID NO 54
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 54
agcactgtca gccgggtgcc tgg                                            23

<210> SEQ ID NO 55
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"
```

<400> SEQUENCE: 55
agcactcaga gccgggtccc ggc                                                     23

<210> SEQ ID NO 56
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for PCR"
      /organism="Artificial Sequence"

<400> SEQUENCE: 56
ccgagcacca ggagccgcgt gc                                                      22

<210> SEQ ID NO 57
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 57
agcacggtca gcctgctgcc ggc                                                     23

<210> SEQ ID NO 58
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 58
gtgaccgtga gcctggtgcc cgg                                                     23

<210> SEQ ID NO 59
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="Primer for PCR"
      /organism="Artificial Sequence"

<400> SEQUENCE: 59
atctacactc tttccctaca cgacgctctt ccgatct                                      37

<210> SEQ ID NO 60
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Primer for PCR"

/organism="Artificial Sequence"

<400> SEQUENCE: 60
tctacactct ttccctacac gacgctcttc cgatct                           36

<210> SEQ ID NO 61
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Primer for PCR"
      /organism="Artificial Sequence"

<400> SEQUENCE: 61
ctacactctt tccctacacg acgctcttcc gatct                            35

<210> SEQ ID NO 62
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="Primer for PCR"
      /organism="Artificial Sequence"

<400> SEQUENCE: 62
tacactcttt ccctacacga cgctcttccg atct                             34

<210> SEQ ID NO 63
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer for PCR"
      /organism="Artificial Sequence"

<400> SEQUENCE: 63
acactctttc cctacacgac gctcttccga tct                              33

<210> SEQ ID NO 64
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Primer for PCR"
      /organism="Artificial Sequence"

<400> SEQUENCE: 64
cactctttcc ctacacgacg ctcttccgat ct                               32

<210> SEQ ID NO 65
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"

/note="Primer for PCR"
/organism="Artificial Sequence"

<400> SEQUENCE: 65
actctttccc tacacgacgc tcttccgatc t    31

<210> SEQ ID NO 66
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Primer for PCR"
      /organism="Artificial Sequence"

<400> SEQUENCE: 66
ctctttccct acacgacgct cttccgatct    30

<210> SEQ ID NO 67
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer for PCR"
      /organism="Artificial Sequence"

<400> SEQUENCE: 67
tctttcccta cacgacgctc ttccgatct    29

<210> SEQ ID NO 68
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 68
ctttccctac acgacgctct tccgatct    28

<210> SEQ ID NO 69
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 69
tttccctaca cgacgctctt ccgatct    27

<210> SEQ ID NO 70
<211> LENGTH: 26
<212> TYPE: DNA
<213> ORGANISM: Artificial Sequence
<220> FEATURE:
<221> NAME/KEY: source
<222> LOCATION: 1..26

<223> OTHER INFORMATION: /mol_type="unassigned DNA"
        /note="Primer for PCR"
        /organism="Artificial Sequence"

<400> SEQUENCE: 70
ttccctacac gacgctcttc cgatct                                              26

<210> SEQ ID NO 71
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
        /note="Primer for PCR"
        /organism="Artificial Sequence"

<400> SEQUENCE: 71
tccctacacg acgctcttcc gatct                                               25

<210> SEQ ID NO 72
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
        /note="Primer for PCR"
        /organism="Artificial Sequence"

<400> SEQUENCE: 72
ccctacacga cgctcttccg atct                                                24

<210> SEQ ID NO 73
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
        /note="Primer for PCR"
        /organism="Artificial Sequence"

<400> SEQUENCE: 73
cctacacgac gctcttccga tct                                                 23

<210> SEQ ID NO 74
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
        /note="Primer for PCR"
        /organism="Artificial Sequence"

<400> SEQUENCE: 74
ctacacgacg ctcttccgat ct                                                  22

<210> SEQ ID NO 75
<211> LENGTH: 21
<212> TYPE: DNA
<213> ORGANISM: Artificial Sequence
<220> FEATURE:
<221> NAME/KEY: source

```
<222> LOCATION: 1..21
<223> OTHER INFORMATION: /mol_type="unassigned DNA"
      /note="Primer for PCR"
      /organism="Artificial Sequence"

<400> SEQUENCE: 75
tacacgacgc tcttccgatc t                                              21

<210> SEQ ID NO 76
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for PCR"
      /organism="Artificial Sequence"

<400> SEQUENCE: 76
acacgacgct cttccgatct                                                20

<210> SEQ ID NO 77
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Primer for PCR"
      /organism="Artificial Sequence"

<400> SEQUENCE: 77
cacgacgctc ttccgatct                                                 19

<210> SEQ ID NO 78
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="Primer for PCR"
      /organism="Artificial Sequence"

<400> SEQUENCE: 78
acgacgctct tccgatct                                                  18

<210> SEQ ID NO 79
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="unassigned DNA"
      /note="Primer for PCR"
      /organism="Artificial Sequence"

<400> SEQUENCE: 79
cgacgctctt ccgatct                                                   17

<210> SEQ ID NO 80
<211> LENGTH: 16
<212> TYPE: DNA
<213> ORGANISM: Artificial Sequence
<220> FEATURE:
```

```
<221> NAME/KEY: source
<222> LOCATION: 1..16
<223> OTHER INFORMATION: /mol_type="unassigned DNA"
      /note="Primer for PCR"
      /organism="Artificial Sequence"

<400> SEQUENCE: 80
gacgctcttc cgatct                                                    16

<210> SEQ ID NO 81
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /mol_type="unassigned DNA"
      /note="Primer for PCR"
      /organism="Artificial Sequence"

<400> SEQUENCE: 81
acgctcttcc gatct                                                     15

<210> SEQ ID NO 82
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 82
cgctcttccg atct                                                      14

<210> SEQ ID NO 83
<211> LENGTH: 13
<212> TYPE: DNA
<213> ORGANISM: Artificial Sequence
<220> FEATURE:
<221> NAME/KEY: source
<222> LOCATION: 1..13
<223> OTHER INFORMATION: /mol_type="unassigned DNA"
      /note="Primer for PCR"
      /organism="Artificial Sequence"

<400> SEQUENCE: 83
gctcttccga tct                                                       13

<210> SEQ ID NO 84
<211> LENGTH: 12
<212> TYPE: DNA
<213> ORGANISM: Artificial Sequence
<220> FEATURE:
<221> NAME/KEY: source
<222> LOCATION: 1..12
<223> OTHER INFORMATION: /mol_type="unassigned DNA"
      /note="Primer for PCR"
      /organism="Artificial Sequence"

<400> SEQUENCE: 84
ctcttccgat ct                                                        12

<210> SEQ ID NO 85
<211> LENGTH: 11
<212> TYPE: DNA
<213> ORGANISM: Artificial Sequence
```

```
<220> FEATURE:
<221> NAME/KEY: source
<222> LOCATION: 1..11
<223> OTHER INFORMATION: /mol_type="unassigned DNA"
      /note="Primer for PCR"
      /organism="Artificial Sequence"

<400> SEQUENCE: 85
tcttccgatc t                                                          11

<210> SEQ ID NO 86
<211> LENGTH: 42
<212> TYPE: DNA
<213> ORGANISM: Artificial Sequence
<220> FEATURE:
<221> NAME/KEY: source
<222> LOCATION: 1..42
<223> OTHER INFORMATION: /mol_type="unassigned DNA"
      /note="Primer for PCR"
      /organism="Artificial Sequence"

<400> SEQUENCE: 86
tacgagatgt gactggagtt cagacgtgtg ctcttccgat ct                        42

<210> SEQ ID NO 87
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="unassigned DNA"
      /note="Primer for PCR"
      /organism="Artificial Sequence"

<400> SEQUENCE: 87
acgagatgtg actggagttc agacgtgtgc tcttccgatc t                         41

<210> SEQ ID NO 88
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="Primer for PCR"
      /organism="Artificial Sequence"

<400> SEQUENCE: 88
cgagatgtga ctggagttca gacgtgtgct cttccgatct                           40

<210> SEQ ID NO 89
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="Primer for PCR"
      /organism="Artificial Sequence"

<400> SEQUENCE: 89
gagatgtgac tggagttcag acgtgtgctc ttccgatct                            39

<210> SEQ ID NO 90
<211> LENGTH: 38
<212> TYPE: DNA
```

```
<213> ORGANISM: Artificial Sequence
<220> FEATURE:
<221> NAME/KEY: source
<222> LOCATION: 1..38
<223> OTHER INFORMATION: /mol_type="unassigned DNA"
      /note="Primer for PCR"
      /organism="Artificial Sequence"

<400> SEQUENCE: 90
agatgtgact ggagttcaga cgtgtgctct tccgatct                           38

<210> SEQ ID NO 91
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="Primer for PCR"
      /organism="Artificial Sequence"

<400> SEQUENCE: 91
gatgtgactg gagttcagac gtgtgctctt ccgatct                            37

<210> SEQ ID NO 92
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Primer for PCR"
      /organism="Artificial Sequence"

<400> SEQUENCE: 92
atgtgactgg agttcagacg tgtgctcttc cgatct                             36

<210> SEQ ID NO 93
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Primer for PCR"
      /organism="Artificial Sequence"

<400> SEQUENCE: 93
tgtgactgga gttcagacgt gtgctcttcc gatct                              35

<210> SEQ ID NO 94
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="Primer for PCR"
      /organism="Artificial Sequence"

<400> SEQUENCE: 94
gtgactggag ttcagacgtg tgctcttccg atct                               34

<210> SEQ ID NO 95
<211> LENGTH: 33
```

```
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer for PCR"
      /organism="Artificial Sequence"

<400> SEQUENCE: 95
tgactggagt tcagacgtgt gctcttccga tct                              33

<210> SEQ ID NO 96
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Primer for PCR"
      /organism="Artificial Sequence"

<400> SEQUENCE: 96
gactggagtt cagacgtgtg ctcttccgat ct                               32

<210> SEQ ID NO 97
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Primer for PCR"
      /organism="Artificial Sequence"

<400> SEQUENCE: 97
actggagttc agacgtgtgc tcttccgatc t                                31

<210> SEQ ID NO 98
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Primer for PCR"
      /organism="Artificial Sequence"

<400> SEQUENCE: 98
ctggagttca gacgtgtgct cttccgatct                                  30

<210> SEQ ID NO 99
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer for PCR"
      /organism="Artificial Sequence"

<400> SEQUENCE: 99
tggagttcag acgtgtgctc ttccgatct                                   29

<210> SEQ ID NO 100
```

```
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 100
ggagttcaga cgtgtgctct tccgatct                                        28

<210> SEQ ID NO 101
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 101
gagttcagac gtgtgctctt ccgatct                                         27

<210> SEQ ID NO 102
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 102
agttcagacg tgtgctcttc cgatct                                          26

<210> SEQ ID NO 103
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 103
gttcagacgt gtgctcttcc gatct                                           25

<210> SEQ ID NO 104
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="Primer for PCR"
      /organism="Artificial Sequence"

<400> SEQUENCE: 104
ttcagacgtg tgctcttccg atct                                            24
```

```
<210> SEQ ID NO 105
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 105
tcagacgtgt gctcttccga tct                                              23

<210> SEQ ID NO 106
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for PCR"
      /organism="Artificial Sequence"

<400> SEQUENCE: 106
cagacgtgtg ctcttccgat ct                                               22

<210> SEQ ID NO 107
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for PCR"
      /organism="Artificial Sequence"

<400> SEQUENCE: 107
agacgtgtgc tcttccgatc t                                                21

<210> SEQ ID NO 108
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for PCR"
      /organism="Artificial Sequence"

<400> SEQUENCE: 108
gacgtgtgct cttccgatct                                                  20

<210> SEQ ID NO 109
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Primer for PCR"
      /organism="Artificial Sequence"

<400> SEQUENCE: 109
acgtgtgctc ttccgatct                                                   19
```

<210> SEQ ID NO 110
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="Primer for PCR"
      /organism="Artificial Sequence"

<400> SEQUENCE: 110
cgtgtgctct tccgatct                                                 18

<210> SEQ ID NO 111
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="unassigned DNA"
      /note="Primer for PCR"
      /organism="Artificial Sequence"

<400> SEQUENCE: 111
gtgtgctctt ccgatct                                                  17

<210> SEQ ID NO 112
<211> LENGTH: 16
<212> TYPE: DNA
<213> ORGANISM: Artificial Sequence
<220> FEATURE:
<221> NAME/KEY: source
<222> LOCATION: 1..16
<223> OTHER INFORMATION: /mol_type="unassigned DNA"
      /note="Primer for PCR"
      /organism="Artificial Sequence"

<400> SEQUENCE: 112
tgtgctcttc cgatct                                                   16

<210> SEQ ID NO 113
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /mol_type="unassigned DNA"
      /note="Primer for PCR"
      /organism="Artificial Sequence"

<400> SEQUENCE: 113
gtgctcttcc gatct                                                    15

<210> SEQ ID NO 114
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 114
tgctcttccg atct                                                     14

<210> SEQ ID NO 115
<211> LENGTH: 13
<212> TYPE: DNA
<213> ORGANISM: Artificial Sequence
<220> FEATURE:
<221> NAME/KEY: source
<222> LOCATION: 1..13
<223> OTHER INFORMATION: /mol_type="unassigned DNA"
        /note="Primer for PCR"
        /organism="Artificial Sequence"

<400> SEQUENCE: 115
gctcttccga tct                                                           13

<210> SEQ ID NO 116
<211> LENGTH: 12
<212> TYPE: DNA
<213> ORGANISM: Artificial Sequence
<220> FEATURE:
<221> NAME/KEY: source
<222> LOCATION: 1..12
<223> OTHER INFORMATION: /mol_type="unassigned DNA"
        /note="Primer for PCR"
        /organism="Artificial Sequence"

<400> SEQUENCE: 116
ctcttccgat ct                                                            12

<210> SEQ ID NO 117
<211> LENGTH: 11
<212> TYPE: DNA
<213> ORGANISM: Artificial Sequence
<220> FEATURE:
<221> NAME/KEY: source
<222> LOCATION: 1..11
<223> OTHER INFORMATION: /mol_type="unassigned DNA"
        /note="Primer for PCR"
        /organism="Artificial Sequence"

<400> SEQUENCE: 117
tcttccgatc t                                                             11

<210> SEQ ID NO 118
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /mol_type="unassigned DNA"
        /note="Primer for PCR"
        /organism="Artificial Sequence"

<400> SEQUENCE: 118
aatgatacgg cgaccaccga gatctacact ctttccctac acgacgctct tccgatct          58

<210> SEQ ID NO 119
<211> LENGTH: 57
<212> TYPE: DNA
<213> ORGANISM: Artificial Sequence
<220> FEATURE:
<221> NAME/KEY: source
<222> LOCATION: 1..57
<223> OTHER INFORMATION: /mol_type="unassigned DNA"
        /note="Primer for PCR"
        /organism="Artificial Sequence"

<400> SEQUENCE: 119
aatgatacgg cgaccaccga gatctacact ctttccctac acgacgctct tccgatc         57

<210> SEQ ID NO 120
<211> LENGTH: 56
<212> TYPE: DNA
<213> ORGANISM: Artificial Sequence
<220> FEATURE:
<221> NAME/KEY: source
<222> LOCATION: 1..56
<223> OTHER INFORMATION: /mol_type="unassigned DNA"
      /note="Primer for PCR"
      /organism="Artificial Sequence"

<400> SEQUENCE: 120
aatgatacgg cgaccaccga gatctacact ctttccctac acgacgctct tccgat          56

<210> SEQ ID NO 121
<211> LENGTH: 55
<212> TYPE: DNA
<213> ORGANISM: Artificial Sequence
<220> FEATURE:
<221> NAME/KEY: source
<222> LOCATION: 1..55
<223> OTHER INFORMATION: /mol_type="unassigned DNA"
      /note="Primer for PCR"
      /organism="Artificial Sequence"

<400> SEQUENCE: 121
aatgatacgg cgaccaccga gatctacact ctttccctac acgacgctct tccga           55

<210> SEQ ID NO 122
<211> LENGTH: 54
<212> TYPE: DNA
<213> ORGANISM: Artificial Sequence
<220> FEATURE:
<221> NAME/KEY: source
<222> LOCATION: 1..54
<223> OTHER INFORMATION: /mol_type="unassigned DNA"
      /note="Primer for PCR"
      /organism="Artificial Sequence"

<400> SEQUENCE: 122
aatgatacgg cgaccaccga gatctacact ctttccctac acgacgctct tccg            54

<210> SEQ ID NO 123
<211> LENGTH: 53
<212> TYPE: DNA
<213> ORGANISM: Artificial Sequence
<220> FEATURE:
<221> NAME/KEY: source
<222> LOCATION: 1..53
<223> OTHER INFORMATION: /mol_type="unassigned DNA"
      /note="Primer for PCR"
      /organism="Artificial Sequence"

<400> SEQUENCE: 123
aatgatacgg cgaccaccga gatctacact ctttccctac acgacgctct tcc             53

<210> SEQ ID NO 124
<211> LENGTH: 52
<212> TYPE: DNA
<213> ORGANISM: Artificial Sequence
<220> FEATURE:
<221> NAME/KEY: source
<222> LOCATION: 1..52
<223> OTHER INFORMATION: /mol_type="unassigned DNA"
      /note="Primer for PCR"
      /organism="Artificial Sequence"

<400> SEQUENCE: 124
aatgatacgg cgaccaccga gatctacact ctttccctac acgacgctct tc        52

<210> SEQ ID NO 125
<211> LENGTH: 51
<212> TYPE: DNA
<213> ORGANISM: Artificial Sequence
<220> FEATURE:
<221> NAME/KEY: source
<222> LOCATION: 1..51
<223> OTHER INFORMATION: /mol_type="unassigned DNA"
      /note="Primer for PCR"
      /organism="Artificial Sequence"

<400> SEQUENCE: 125
aatgatacgg cgaccaccga gatctacact ctttccctac acgacgctct t         51

<210> SEQ ID NO 126
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Primer for PCR"
      /organism="Artificial Sequence"

<400> SEQUENCE: 126
aatgatacgg cgaccaccga gatctacact ctttccctac acgacgctct           50

<210> SEQ ID NO 127
<211> LENGTH: 49
<212> TYPE: DNA
<213> ORGANISM: Artificial Sequence
<220> FEATURE:
<221> NAME/KEY: source
<222> LOCATION: 1..49
<223> OTHER INFORMATION: /mol_type="unassigned DNA"
      /note="Primer for PCR"
      /organism="Artificial Sequence"

<400> SEQUENCE: 127
aatgatacgg cgaccaccga gatctacact ctttccctac acgacgctc            49

<210> SEQ ID NO 128
<211> LENGTH: 48
<212> TYPE: DNA
<213> ORGANISM: Artificial Sequence
<220> FEATURE:
<221> NAME/KEY: source
<222> LOCATION: 1..48
<223> OTHER INFORMATION: /mol_type="unassigned DNA"
      /note="Primer for PCR"
      /organism="Artificial Sequence"

<400> SEQUENCE: 128
aatgatacgg cgaccaccga gatctacact ctttccctac acgacgct             48

<210> SEQ ID NO 129
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="Primer for PCR"
      /organism="Artificial Sequence"

<400> SEQUENCE: 129
aatgatacgg cgaccaccga gatctacact ctttccctac acgacgc                    47

<210> SEQ ID NO 130
<211> LENGTH: 46
<212> TYPE: DNA
<213> ORGANISM: Artificial Sequence
<220> FEATURE:
<221> NAME/KEY: source
<222> LOCATION: 1..46
<223> OTHER INFORMATION: /mol_type="unassigned DNA"
      /note="Primer for PCR"
      /organism="Artificial Sequence"

<400> SEQUENCE: 130
aatgatacgg cgaccaccga gatctacact ctttccctac acgacg                     46

<210> SEQ ID NO 131
<211> LENGTH: 45
<212> TYPE: DNA
<213> ORGANISM: Artificial Sequence
<220> FEATURE:
<221> NAME/KEY: source
<222> LOCATION: 1..45
<223> OTHER INFORMATION: /mol_type="unassigned DNA"
      /note="Primer for PCR"
      /organism="Artificial Sequence"

<400> SEQUENCE: 131
aatgatacgg cgaccaccga gatctacact ctttccctac acgac                      45

<210> SEQ ID NO 132
<211> LENGTH: 44
<212> TYPE: DNA
<213> ORGANISM: Artificial Sequence
<220> FEATURE:
<221> NAME/KEY: source
<222> LOCATION: 1..44
<223> OTHER INFORMATION: /mol_type="unassigned DNA"
      /note="Primer for PCR"
      /organism="Artificial Sequence"

<400> SEQUENCE: 132
aatgatacgg cgaccaccga gatctacact ctttccctac acga                       44

<210> SEQ ID NO 133
<211> LENGTH: 43
<212> TYPE: DNA
<213> ORGANISM: Artificial Sequence
<220> FEATURE:
<221> NAME/KEY: source
<222> LOCATION: 1..43
<223> OTHER INFORMATION: /mol_type="unassigned DNA"
      /note="Primer for PCR"
      /organism="Artificial Sequence"

<400> SEQUENCE: 133
aatgatacgg cgaccaccga gatctacact ctttccctac acg                        43

<210> SEQ ID NO 134
<211> LENGTH: 42
<212> TYPE: DNA
<213> ORGANISM: Artificial Sequence
<220> FEATURE:
<221> NAME/KEY: source
<222> LOCATION: 1..42
<223> OTHER INFORMATION: /mol_type="unassigned DNA"
      /note="Primer for PCR"
      /organism="Artificial Sequence"

<400> SEQUENCE: 134
aatgatacgg cgaccaccga gatctacact ctttccctac ac                42

<210> SEQ ID NO 135
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="unassigned DNA"
      /note="Primer for PCR"
      /organism="Artificial Sequence"

<400> SEQUENCE: 135
aatgatacgg cgaccaccga gatctacact ctttccctac a                 41

<210> SEQ ID NO 136
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="Primer for PCR"
      /organism="Artificial Sequence"

<400> SEQUENCE: 136
aatgatacgg cgaccaccga gatctacact ctttccctac                   40

<210> SEQ ID NO 137
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="Primer for PCR"
      /organism="Artificial Sequence"

<400> SEQUENCE: 137
aatgatacgg cgaccaccga gatctacact ctttcccta                    39

<210> SEQ ID NO 138
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="unassigned DNA"
      /note="Primer for PCR"
      /organism="Artificial Sequence"

<400> SEQUENCE: 138
aatgatacgg cgaccaccga gatctacact ctttccct                     38

<210> SEQ ID NO 139
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="Primer for PCR"

/organism="Artificial Sequence"

<400> SEQUENCE: 139
aatgatacgg cgaccaccga gatctacact ctttccc                                    37

<210> SEQ ID NO 140
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Primer for PCR"
      /organism="Artificial Sequence"

<400> SEQUENCE: 140
aatgatacgg cgaccaccga gatctacact ctttcc                                     36

<210> SEQ ID NO 141
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Primer for PCR"
      /organism="Artificial Sequence"

<400> SEQUENCE: 141
aatgatacgg cgaccaccga gatctacact ctttc                                      35

<210> SEQ ID NO 142
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="Primer for PCR"
      /organism="Artificial Sequence"

<400> SEQUENCE: 142
aatgatacgg cgaccaccga gatctacact cttt                                       34

<210> SEQ ID NO 143
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer for PCR"
      /organism="Artificial Sequence"

<400> SEQUENCE: 143
aatgatacgg cgaccaccga gatctacact ctt                                        33

<210> SEQ ID NO 144
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"

-continued

/note="Primer for PCR"
/organism="Artificial Sequence"

<400> SEQUENCE: 144
aatgatacgg cgaccaccga gatctacact ct                                    32

<210> SEQ ID NO 145
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Primer for PCR"
      /organism="Artificial Sequence"

<400> SEQUENCE: 145
aatgatacgg cgaccaccga gatctacact c                                     31

<210> SEQ ID NO 146
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Primer for PCR"
      /organism="Artificial Sequence"

<400> SEQUENCE: 146
aatgatacgg cgaccaccga gatctacact                                       30

<210> SEQ ID NO 147
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 147
aatgatacgg cgaccaccga gatctaca                                         28

<210> SEQ ID NO 148
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 148
aatgatacgg cgaccaccga gatctac                                          27

<210> SEQ ID NO 149
<211> LENGTH: 26
<212> TYPE: DNA
<213> ORGANISM: Artificial Sequence
<220> FEATURE:
<221> NAME/KEY: source
<222> LOCATION: 1..26

```
<223> OTHER INFORMATION: /mol_type="unassigned DNA"
      /note="Primer for PCR"
      /organism="Artificial Sequence"

<400> SEQUENCE: 149
aatgatacgg cgaccaccga gatcta                                      26

<210> SEQ ID NO 150
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /mol_type="unassigned DNA"
      /note="Primer for PCR"
      /organism="Artificial Sequence"

<400> SEQUENCE: 150
caagcagaag acggcatacg agatgtgact ggagttcaga cgtgtgctct tccgatct    58

<210> SEQ ID NO 151
<211> LENGTH: 57
<212> TYPE: DNA
<213> ORGANISM: Artificial Sequence
<220> FEATURE:
<221> NAME/KEY: source
<222> LOCATION: 1..57
<223> OTHER INFORMATION: /mol_type="unassigned DNA"
      /note="Primer for PCR"
      /organism="Artificial Sequence"

<400> SEQUENCE: 151
caagcagaag acggcatacg agatgtgact ggagttcaga cgtgtgctct tccgatc     57

<210> SEQ ID NO 152
<211> LENGTH: 56
<212> TYPE: DNA
<213> ORGANISM: Artificial Sequence
<220> FEATURE:
<221> NAME/KEY: source
<222> LOCATION: 1..56
<223> OTHER INFORMATION: /mol_type="unassigned DNA"
      /note="Primer for PCR"
      /organism="Artificial Sequence"

<400> SEQUENCE: 152
caagcagaag acggcatacg agatgtgact ggagttcaga cgtgtgctct tccgat      56

<210> SEQ ID NO 153
<211> LENGTH: 55
<212> TYPE: DNA
<213> ORGANISM: Artificial Sequence
<220> FEATURE:
<221> NAME/KEY: source
<222> LOCATION: 1..55
<223> OTHER INFORMATION: /mol_type="unassigned DNA"
      /note="Primer for PCR"
      /organism="Artificial Sequence"

<400> SEQUENCE: 153
caagcagaag acggcatacg agatgtgact ggagttcaga cgtgtgctct tccga       55

<210> SEQ ID NO 154
<211> LENGTH: 54
<212> TYPE: DNA
<213> ORGANISM: Artificial Sequence
<220> FEATURE:
<221> NAME/KEY: source
```

```
<222> LOCATION: 1..54
<223> OTHER INFORMATION: /mol_type="unassigned DNA"
      /note="Primer for PCR"
      /organism="Artificial Sequence"

<400> SEQUENCE: 154
caagcagaag acggcatacg agatgtgact ggagttcaga cgtgtgctct tccg         54

<210> SEQ ID NO 155
<211> LENGTH: 53
<212> TYPE: DNA
<213> ORGANISM: Artificial Sequence
<220> FEATURE:
<221> NAME/KEY: source
<222> LOCATION: 1..53
<223> OTHER INFORMATION: /mol_type="unassigned DNA"
      /note="Primer for PCR"
      /organism="Artificial Sequence"

<400> SEQUENCE: 155
caagcagaag acggcatacg agatgtgact ggagttcaga cgtgtgctct tcc          53

<210> SEQ ID NO 156
<211> LENGTH: 52
<212> TYPE: DNA
<213> ORGANISM: Artificial Sequence
<220> FEATURE:
<221> NAME/KEY: source
<222> LOCATION: 1..52
<223> OTHER INFORMATION: /mol_type="unassigned DNA"
      /note="Primer for PCR"
      /organism="Artificial Sequence"

<400> SEQUENCE: 156
caagcagaag acggcatacg agatgtgact ggagttcaga cgtgtgctct tc           52

<210> SEQ ID NO 157
<211> LENGTH: 51
<212> TYPE: DNA
<213> ORGANISM: Artificial Sequence
<220> FEATURE:
<221> NAME/KEY: source
<222> LOCATION: 1..51
<223> OTHER INFORMATION: /mol_type="unassigned DNA"
      /note="Primer for PCR"
      /organism="Artificial Sequence"

<400> SEQUENCE: 157
caagcagaag acggcatacg agatgtgact ggagttcaga cgtgtgctct t            51

<210> SEQ ID NO 158
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Primer for PCR"
      /organism="Artificial Sequence"

<400> SEQUENCE: 158
caagcagaag acggcatacg agatgtgact ggagttcaga cgtgtgctct              50

<210> SEQ ID NO 159
<211> LENGTH: 49
<212> TYPE: DNA
<213> ORGANISM: Artificial Sequence
<220> FEATURE:
```

```
<221> NAME/KEY: source
<222> LOCATION: 1..49
<223> OTHER INFORMATION: /mol_type="unassigned DNA"
      /note="Primer for PCR"
      /organism="Artificial Sequence"

<400> SEQUENCE: 159
caagcagaag acggcatacg agatgtgact ggagttcaga cgtgtgctc              49

<210> SEQ ID NO 160
<211> LENGTH: 48
<212> TYPE: DNA
<213> ORGANISM: Artificial Sequence
<220> FEATURE:
<221> NAME/KEY: source
<222> LOCATION: 1..48
<223> OTHER INFORMATION: /mol_type="unassigned DNA"
      /note="Primer for PCR"
      /organism="Artificial Sequence"

<400> SEQUENCE: 160
caagcagaag acggcatacg agatgtgact ggagttcaga cgtgtgct               48

<210> SEQ ID NO 161
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="Primer for PCR"
      /organism="Artificial Sequence"

<400> SEQUENCE: 161
caagcagaag acggcatacg agatgtgact ggagttcaga cgtgtgc                47

<210> SEQ ID NO 162
<211> LENGTH: 46
<212> TYPE: DNA
<213> ORGANISM: Artificial Sequence
<220> FEATURE:
<221> NAME/KEY: source
<222> LOCATION: 1..46
<223> OTHER INFORMATION: /mol_type="unassigned DNA"
      /note="Primer for PCR"
      /organism="Artificial Sequence"

<400> SEQUENCE: 162
caagcagaag acggcatacg agatgtgact ggagttcaga cgtgtg                 46

<210> SEQ ID NO 163
<211> LENGTH: 45
<212> TYPE: DNA
<213> ORGANISM: Artificial Sequence
<220> FEATURE:
<221> NAME/KEY: source
<222> LOCATION: 1..45
<223> OTHER INFORMATION: /mol_type="unassigned DNA"
      /note="Primer for PCR"
      /organism="Artificial Sequence"

<400> SEQUENCE: 163
caagcagaag acggcatacg agatgtgact ggagttcaga cgtgt                  45

<210> SEQ ID NO 164
<211> LENGTH: 44
<212> TYPE: DNA
<213> ORGANISM: Artificial Sequence
```

```
<220> FEATURE:
<221> NAME/KEY: source
<222> LOCATION: 1..44
<223> OTHER INFORMATION: /mol_type="unassigned DNA"
      /note="Primer for PCR"
      /organism="Artificial Sequence"

<400> SEQUENCE: 164
caagcagaag acggcatacg agatgtgact ggagttcaga cgtg            44

<210> SEQ ID NO 165
<211> LENGTH: 43
<212> TYPE: DNA
<213> ORGANISM: Artificial Sequence
<220> FEATURE:
<221> NAME/KEY: source
<222> LOCATION: 1..43
<223> OTHER INFORMATION: /mol_type="unassigned DNA"
      /note="Primer for PCR"
      /organism="Artificial Sequence"

<400> SEQUENCE: 165
caagcagaag acggcatacg agatgtgact ggagttcaga cgt             43

<210> SEQ ID NO 166
<211> LENGTH: 42
<212> TYPE: DNA
<213> ORGANISM: Artificial Sequence
<220> FEATURE:
<221> NAME/KEY: source
<222> LOCATION: 1..42
<223> OTHER INFORMATION: /mol_type="unassigned DNA"
      /note="Primer for PCR"
      /organism="Artificial Sequence"

<400> SEQUENCE: 166
caagcagaag acggcatacg agatgtgact ggagttcaga cg              42

<210> SEQ ID NO 167
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="unassigned DNA"
      /note="Primer for PCR"
      /organism="Artificial Sequence"

<400> SEQUENCE: 167
caagcagaag acggcatacg agatgtgact ggagttcaga c               41

<210> SEQ ID NO 168
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="Primer for PCR"
      /organism="Artificial Sequence"

<400> SEQUENCE: 168
caagcagaag acggcatacg agatgtgact ggagttcaga                 40

<210> SEQ ID NO 169
<211> LENGTH: 39
<212> TYPE: DNA
```

```
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="Primer for PCR"
      /organism="Artificial Sequence"

<400> SEQUENCE: 169
caagcagaag acggcatacg agatgtgact ggagttcag                              39

<210> SEQ ID NO 170
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="unassigned DNA"
      /note="Primer for PCR"
      /organism="Artificial Sequence"

<400> SEQUENCE: 170
caagcagaag acggcatacg agatgtgact ggagttca                               38

<210> SEQ ID NO 171
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="Primer for PCR"
      /organism="Artificial Sequence"

<400> SEQUENCE: 171
caagcagaag acggcatacg agatgtgact ggagttc                                37

<210> SEQ ID NO 172
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Primer for PCR"
      /organism="Artificial Sequence"

<400> SEQUENCE: 172
caagcagaag acggcatacg agatgtgact ggagtt                                 36

<210> SEQ ID NO 173
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Primer for PCR"
      /organism="Artificial Sequence"

<400> SEQUENCE: 173
caagcagaag acggcatacg agatgtgact ggagt                                  35

<210> SEQ ID NO 174
<211> LENGTH: 34
```

```
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="Primer for PCR"
      /organism="Artificial Sequence"

<400> SEQUENCE: 174
caagcagaag acggcatacg agatgtgact ggag                              34

<210> SEQ ID NO 175
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer for PCR"
      /organism="Artificial Sequence"

<400> SEQUENCE: 175
caagcagaag acggcatacg agatgtgact gga                               33

<210> SEQ ID NO 176
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Primer for PCR"
      /organism="Artificial Sequence"

<400> SEQUENCE: 176
caagcagaag acggcatacg agatgtgact gg                                32

<210> SEQ ID NO 177
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Primer for PCR"
      /organism="Artificial Sequence"

<400> SEQUENCE: 177
caagcagaag acggcatacg agatgtgact g                                 31

<210> SEQ ID NO 178
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Primer for PCR"
      /organism="Artificial Sequence"

<400> SEQUENCE: 178
caagcagaag acggcatacg agatgtgact                                   30

<210> SEQ ID NO 179
```

```
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer for PCR"
      /organism="Artificial Sequence"

<400> SEQUENCE: 179
caagcagaag acggcatacg agatgtgac                                  29

<210> SEQ ID NO 180
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 180
caagcagaag acggcatacg agatgtga                                   28

<210> SEQ ID NO 181
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 181
caagcagaag acggcatacg agatgtg                                    27

<210> SEQ ID NO 182
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 182
caagcagaag acggcatacg agatgt                                     26

<210> SEQ ID NO 183
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 183
ttattccttc acctacacac cctgc                                      25
```

<210> SEQ ID NO 184
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 184
agcactgtca gccgggtgcc tgg                                              23

<210> SEQ ID NO 185
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 185
cgctcttccg atct                                                        14

<210> SEQ ID NO 186
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 186
tgctcttccg atct                                                        14

<210> SEQ ID NO 187
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /mol_type="unassigned DNA"
      /note="Primer for PCR"
      /organism="Artificial Sequence"

<400> SEQUENCE: 187
aatgatacgg cgaccaccga gatctacact ctttccctac acgacgctct tccgatct        58

<210> SEQ ID NO 188
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /mol_type="unassigned DNA"
      /note="Primer for PCR"
      /organism="Artificial Sequence"

<400> SEQUENCE: 188
caagcagaag acggcatacg agatgtgact ggagttcaga cgtgtgctct tccgatct        58

```
<210> SEQ ID NO 189
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 189
ttcactctga agatccggtc cacaa                                         25

<210> SEQ ID NO 190
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer for PCR"
      /organism="Artificial Sequence"

<400> SEQUENCE: 190
cacttaaatc ttcacatcaa ttccctgg                                      28

<210> SEQ ID NO 191
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 191
ttaaaccttc acctacacgc cctgc                                         25

<210> SEQ ID NO 192
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 192
ttattccttc acctacacac cctgc                                         25

<210> SEQ ID NO 193
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 193
cgctctgaga tgaatgtgag caccttg                                       27
```

<210> SEQ ID NO 194
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 194
tgctctgaga tgaatgtgag tgccttg                                27

<210> SEQ ID NO 195
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 195
agctctgagc tgaatgtgaa cgccttg                                27

<210> SEQ ID NO 196
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 196
ttctcgctca ggctggagtc ggctg                                  25

<210> SEQ ID NO 197
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 197
ttcctgctgg ggttggagtc ggctg                                  25

<210> SEQ ID NO 198
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 198
ttccccctca cgttggcgtc tgctg                                              25

<210> SEQ ID NO 199
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for PCR"
      /organism="Artificial Sequence"

<400> SEQUENCE: 199
ccgctcaggc tgctgtcggc tg                                                 22

<210> SEQ ID NO 200
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 200
ttcccgctca ggctggagtt ggctg                                              25

<210> SEQ ID NO 201
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 201 ttcccccctca agctggagtc agctg                                             25

<210> SEQ ID NO 202
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 202
ttcccactca ggctggtgtc ggctg                                              25

<210> SEQ ID NO 203
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 203
ttcccgctca ggctggagtc agctg                                        25

<210> SEQ ID NO 204
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 204
tccactctga agttccagcg cacac                                        25

<210> SEQ ID NO 205
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 205
tccactctga cgatccagcg cacac                                        25

<210> SEQ ID NO 206
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 206
tctactctga agatccagcg cacag                                        25

<210> SEQ ID NO 207
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 207
tccactctga agatccagcg cacag                                        25

<210> SEQ ID NO 208
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

```
<400> SEQUENCE: 208
tccactctga cgatccagcg cacag                                              25

<210> SEQ ID NO 209
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 209
tccactctga cgattcagcg cacag                                              25

<210> SEQ ID NO 210
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 210
tccactctga agatccagcg cacac                                              25

<210> SEQ ID NO 211
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 211
tccaccttgg agatccagcg cacag                                              25

<210> SEQ ID NO 212
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer for PCR"
      /organism="Artificial Sequence"

<400> SEQUENCE: 212
cactctgaac taaacctgag ctctctg                                            27

<210> SEQ ID NO 213
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"
```

-continued

<400> SEQUENCE: 213
ctccccctca ctctggagtc tgctg                                              25

<210> SEQ ID NO 214
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 214
ttccccctca ctctggagtc agcta                                              25

<210> SEQ ID NO 215
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 215
ttcctcctca ctctggagtc cgcta                                              25

<210> SEQ ID NO 216
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 216
aaaggagtag actccactct caaga                                              25

<210> SEQ ID NO 217
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 217
tccactctga agatccagcc ctcag                                              25

<210> SEQ ID NO 218
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"

/organism="Artificial Sequence"

<400> SEQUENCE: 218
tctgaactga acatgagctc cttgg                                             25

<210> SEQ ID NO 219
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 219
tctactctga aggtgcagcc tgcag                                             25

<210> SEQ ID NO 220
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 220
aacttccaat ccaggaggcc gaaca                                             25

<210> SEQ ID NO 221
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 221
tgtagccttg agatccaggc tacga                                             25

<210> SEQ ID NO 222
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 222
tcttccacgc tgaagatcca tcccg                                             25

<210> SEQ ID NO 223
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"

-continued

/note="Primer for PCR"
/organism="Artificial Sequence"

<400> SEQUENCE: 223
agcatcctga ggatccagca ggtag                               25

<210> SEQ ID NO 224
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 224
tttcctctca ctgtgacatc ggccc                               25

<210> SEQ ID NO 225
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 225
ttgtccactc tgacagtgac cagtg                               25

<210> SEQ ID NO 226
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 226
tgcagcctgg caatcctgtc ctcag                               25

<210> SEQ ID NO 227
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 227
ttctccctgt ccctagagtc tgccat                              26

<210> SEQ ID NO 228
<211> LENGTH: 25
<212> TYPE: DNA
<213> ORGANISM: Artificial Sequence
<220> FEATURE:
<221> NAME/KEY: source
<222> LOCATION: 1..25

```
<223> OTHER INFORMATION: /mol_type="unassigned DNA"
      /note="Primer for PCR"
      /organism="Artificial Sequence"

<400> SEQUENCE: 228
tttcccctga ccctggagtc tgcca                                           25

<210> SEQ ID NO 229
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 229 ttcccccctga tcctggagtc gccca                                          25

<210> SEQ ID NO 230
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 230
ttctccctga ttctggagtc cgcca                                           25

<210> SEQ ID NO 231
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 231
ttctcaactc tgactgtgag caaca                                           25

<210> SEQ ID NO 232
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 232
cagttcatcc tgagttctaa gaagc                                           25

<210> SEQ ID NO 233
<211> LENGTH: 26
<212> TYPE: DNA
<213> ORGANISM: Artificial Sequence
<220> FEATURE:
<221> NAME/KEY: source
```

```
<222> LOCATION: 1..26
<223> OTHER INFORMATION: /mol_type="unassigned DNA"
      /note="Primer for PCR"
      /organism="Artificial Sequence"

<400> SEQUENCE: 233
ttacctacaa ctgtgagtct ggtgcc                                   26

<210> SEQ ID NO 234
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 234
cctacaacgg ttaacctggt ccccg                                    25

<210> SEQ ID NO 235
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 235
cctacaacag tgagccaact tccct                                    25

<210> SEQ ID NO 236
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for PCR"
      /organism="Artificial Sequence"

<400> SEQUENCE: 236
cccaagacag agagctgggt tccact                                   26

<210> SEQ ID NO 237
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 237
ttacctagga tggagagtcg agtcc                                    25

<210> SEQ ID NO 238
<211> LENGTH: 25
<212> TYPE: DNA
<213> ORGANISM: Artificial Sequence
<220> FEATURE:
```

```
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 238
cctgtcacag tgagcctggt cccat                                  25

<210> SEQ ID NO 239
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 239
cctgtcacag tgagcctggt cccgt                                  25

<210> SEQ ID NO 240
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 240
cctagcacgg tgagccgtgt ccc                                    23

<210> SEQ ID NO 241
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for PCR"
      /organism="Artificial Sequence"

<400> SEQUENCE: 241
ttacccagta cggtcagcct agagc                                  25

<210> SEQ ID NO 242
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 242
agcactgtca gccgggtgcc tgg                                    23

<210> SEQ ID NO 243
<211> LENGTH: 23
<212> TYPE: DNA
<213> ORGANISM: Artificial Sequence
```

```
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 243
agcactcaga gccgggtccc ggc                                    23

<210> SEQ ID NO 244
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for PCR"
      /organism="Artificial Sequence"

<400> SEQUENCE: 244
ccgagcacca ggagccgcgt gc                                     22

<210> SEQ ID NO 245
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 245
agcacggtca gcctgctgcc ggc                                    23

<210> SEQ ID NO 246
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer for PCR"
      /organism="Artificial Sequence"

<400> SEQUENCE: 246
gtgaccgtga gcctggtgcc cgg                                    23

<210> SEQ ID NO 247
<211> LENGTH: 13
<212> TYPE: DNA
<213> ORGANISM: Artificial Sequence
<220> FEATURE:
<221> NAME/KEY: source
<222> LOCATION: 1..13
<223> OTHER INFORMATION: /mol_type="unassigned DNA"
      /note="Primer for PCR"
      /organism="Artificial Sequence"

<400> SEQUENCE: 247
gctcttccga tct                                               13

<210> SEQ ID NO 248
<211> LENGTH: 15
<212> TYPE: DNA
```

```
<213> ORGANISM: Artificial Sequence
<220> FEATURE:
<221> NAME/KEY: source
<222> LOCATION: 1..15
<223> OTHER INFORMATION: /mol_type="unassigned DNA"
      /note="Primer for PCR"
      /organism="Artificial Sequence"

<400> SEQUENCE: 248
acctacacac cctgc                                              15

<210> SEQ ID NO 249
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 249
agccgggtgc ctgg                                               14

<210> SEQ ID NO 250
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 250
cgctcttccg atct                                               14

<210> SEQ ID NO 251
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="Primer for PCR"
      /organism="Artificial Sequence"

<400> SEQUENCE: 251
tgctcttccg atct                                               14
```